(12) United States Patent  
Fan

(10) Patent No.: US 11,331,319 B2  
(45) Date of Patent: May 17, 2022

(54) COMBINATION TREATMENT FOR NEUROPSYCHIATRIC DISORDERS

(71) Applicant: UNIVERSITY OF MASSACHUSETTS, Boston, MA (US)

(72) Inventor: Xiaoduo Fan, Andover, MA (US)

(73) Assignee: UNIVERSITY OF MASSACHUSETTS, Boston, MA (US)

( * ) Notice: Subject to any disclaimer, the term of this patent is extended or adjusted under 35 U.S.C. 154(b) by 63 days.

(21) Appl. No.: 16/651,001

(22) PCT Filed: Sep. 27, 2018

(86) PCT No.: PCT/US2018/053217  
§ 371 (c)(1),  
(2) Date: Mar. 26, 2020

(87) PCT Pub. No.: WO2019/067782  
PCT Pub. Date: Apr. 4, 2019

(65) Prior Publication Data  
US 2020/0306250 A1 Oct. 1, 2020

Related U.S. Application Data

(60) Provisional application No. 62/564,642, filed on Sep. 28, 2017.

(51) Int. Cl.  
*A61K 31/498* (2006.01)  
*A61K 31/19* (2006.01)  
*A61P 25/18* (2006.01)  
*A61P 25/24* (2006.01)  
*A61K 31/519* (2006.01)  
*A61K 31/198* (2006.01)

(52) U.S. Cl.  
CPC .......... *A61K 31/519* (2013.01); *A61K 31/198* (2013.01); *A61P 25/18* (2018.01)

(58) Field of Classification Search  
CPC ....... A61K 31/498; A61K 31/19; A61P 25/18; A61P 25/24  
USPC ................................................ 514/249, 565  
See application file for complete search history.

(56) References Cited

U.S. PATENT DOCUMENTS

| | | | |
|---|---|---|---|
| 5,705,188 A | 1/1998 | Junichi et al. | 424/450 |
| 6,323,218 B1 | 11/2001 | Bush et al. | 514/311 |
| 2006/0252707 A1 | 11/2006 | Deby et al. | 514/171 |
| 2009/0176790 A1 | 7/2009 | Kakkis | 514/249 |

FOREIGN PATENT DOCUMENTS

| | | |
|---|---|---|
| CN | 106109449 A | 11/2016 |
| WO | WO/1997/030731 | 8/1997 |

OTHER PUBLICATIONS

Akbarian, S. (2010) "The molecular pathology of schizophrenia—focus on histone and DNA modifications," *Brain Research Bulletin* 83(3-4), 103-107.

American Psychiatry Association. (2013) "Bipolar and Related Disorders," in *Diagnostic and Statistical Manual of Mental Disorders (5th ed.)*, pp. 123-154, American Psychiatric Publishing, Arlington.

American Psychiatry Association. (2013) "Disruptive Mood Dysregulation Disorder," in *Diagnostic and Statistical Manual of Mental Disorders (5th ed.)*, pp. 156-168, American Psychiatric Publishing, Arlington.

American Psychiatry Association. (2013) "Schizotypal Personality Disorder," in *Diagnostic and Statistical Manual of Mental Disorders (5th ed.)*, pp. 655-659, American Psychiatric Publishing, Arlington.

Amin, A. R. et al. (1996) "A novel mechanism of action of tetracyclines: effects on nitric oxide synthases," *Proceedings of the National Academy of Sciences of the United States of America* 93(2A), 14014-14019.

Amin, A. R. et al. (1997) "Post-transcriptional regulation of inducible nitric oxide synthase mRNA in murine macrophages by doxycycline and chemically modified tetracyclines," *FEBS Letters* 410(2-3), 259-264.

Anderson, I. M et al. (2012) "Bipolar disorder," *BMJ345*, e8508.

Andreasen, N. C. (1982) "Negative symptoms in schizophrenia. Definition and reliability," *Archives of General Psychiatry* 39(7), 784-788.

Baba, H. et al. (2004) "Expression of nNOS and soluble guanylate cyclase in schizophrenic brain," *Neuroreport* 15(A), 677-680.

Bernstein, H. G. et al. (2005) "The many faces of nitric oxide in schizophrenia. A review," *Schizophrenia Research* 78(1), 69-86.

Bernstein, H. G. et al. (2001) "Increased No. of nitric oxide synthase immunoreactive Purkinje cells and dentate nucleus neurons in schizophrenia," *Journal of Neurocytology* 30(8), 661-670.

Bitanihirwe, B. K. Y. et al. (2011) "Oxidative stress in schizophrenia: an integrated approach," *Neuroscience and Biobehavioral Reviews* 35(3), 878-893.

Bombin, I. et al. (2005) "Significance and Meaning of Neurological Signs in Schizophrenia: Two Decades Later," *Schizophrenia Bulletin* 31(4), 962-977.

Calabrese, V. et al. (2007) "Nitric oxide in the central nervous system: neuroprotection versus neurotoxicity," *Nature Reviews. Neuroscience* 8(10), 766-775.

Caravaggio, F. et al. (2016) "The effect of striatal dopamine depletion on striatal and cortical glutamate: A mini-review," *Progress in Neuro-Psychopharmacology & Biological Psychiatry* 65, 49-53.

(Continued)

*Primary Examiner* — Raymond J Henley, III  
(74) *Attorney, Agent, or Firm* — Medlen & Carroll, LLP

(57) ABSTRACT

Given its various activities in the brain, nitric oxide (NO) has been associated with various neuropsychiatric diseases and/or neuropsychiatric disorders, including schizophrenia. In fact, evidence has been accumulating to show that abnormalities in NO levels are associated with schizophrenia. Among a number of NO's neural mechanisms associated with schizophrenia, its role as a second messenger of NMDA receptor activation, which interacts with both dopaminergic and serotonergic pathways, has been of particular focus. It demonstrated herein that a combined administration of nitric oxide synthase substrates and co-factors display antineuropsychiatric activity and cognitive benefit by re-establishing homeostatic nitric oxide production.

18 Claims, 4 Drawing Sheets

(56) References Cited

OTHER PUBLICATIONS

Cardno, A. G. et al. (1999) "Heritability Estimates for Psychotic Disorders: The Maudsley Twin Psychosis Series," *Archives of General Psychiatry* 56(2), 162-168.
Caspi, A. et al. (2004) "Treatment-refractory schizophrenia," *Dialogues in clinical neuroscience* 6(1), 61-70.
Chase, K. A. et al. (2013) "Histone methylation at H3K9: evidence for a restrictive epigenome in schizophrenia," *Schizophrenia Research* 149(1-3), 15-20.
Chaudhry, I. B. et al. (2012) "Minocycline benefits negative symptoms in early schizophrenia: a randomised double-blind placebo-controlled clinical trial in patients on standard treatment," *Journal of Psychopharmacology* 26(9), 1185-1193.
Cohen, S. M. et al. (2015) "The impact of Nmd A receptor hypofunction on GABAergic neurons in the pathophysiology of schizophrenia," *Schizophrenia Research* 167(1-3), 98-107.
Cortas, N. K. et al. (1990) "Determination of inorganic nitrate in serum and urine by a kinetic cadmium-reduction method," *Clinical Chemistry* 36(8 Pt 1), 1440-1443.
Coyle, J. T. (2013) "Nitric oxide and symptom reduction in schizophrenia," *JAMA Psychiatry* 70(7), 664-665.
Doyle, C. A. et al. (1995) "Application of [3H]L-N(G)-nitroarginine labelling to measure cerebellar nitric oxide synthase inpatients with schizophrenia," *Neuroscience Letters* 202(1-2), 49-52.
Driessen, E. et al. (2010) "Cognitive behavioral therapy for mood disorders: efficacy, moderators and mediators," *The Psychiatric clinics of North America* 33(3), 537-555.
Förstermann, U. et al. (2011) "Therapeutic effect of enhancing endothelial nitric oxide synthase (eNOS) expression and preventing eNOS uncoupling," *British Journal of Pharmacology* 164(2), 213-223.
Fournier, J. C. et al. (2010) "Antidepressant Drug Effects and Depression Severity: A Patient-Level Meta-analysis," *JAMA* 303(1), 47-53.
Freedman, R. et al. (2000) "The alpha7-nicotinic acetylcholine receptor and the pathology of hippocampal interneurons in schizophrenia," *Journal of Chemical Neuroanatomy* 20(3-4), 299-306.
Frye, R. E. et al. (2010) "Tetrahydrobiopterin as a novel therapeutic intervention for autism," *Neurotherapeutics* 7(3), 241-249.
Garrido-Mesa, N. et al. (2013) "What is behind the non-antibiotic properties of minocycline?," *Pharmacological Research* 67(1), 18-30.
Garthwaite, J. et al. (1988) "Endothelium-derived relaxing factor release on activation of NMDA receptors suggests role as intercellular messenger in the brain," *Nature* 336(6197), 385-388.
Ghanizadeh, A. et al. (2014) "Minocycline as add-on treatment decreases the negative symptoms of schizophrenia; a randomized placebo-controlled clinical trial," *Recent Patents on Inflammation & Allergy Drug Discovery* 8(3), 211-215.
Guix, F. X. et al. (2005) "The physiology and pathophysiology of nitric oxide in the brain," *Progress in Neurobiology* 76(2), 126-152.
Haley, J. E. et al. (1992) "The role of nitric oxide in hippocampal long-term potentiation," *Neuron* 8(2), 211-216.
Hallak, J. E. C. et al. (2013) "Rapid Improvement of Acute Schizophrenia Symptoms After Intravenous Sodium Nitroprusside: A Randomized, Double-blind, Placebo-Controlled Trial," *JAMA Psychiatry* 70(7), 668-676.
Hars, B. (1999) "Endogenous nitric oxide in the rat pons promotes sleep," *Brain Research* 816(1), 209-219.
Heinrichs, D. W. et al. (1988) "Significance and meaning of neurological signs in schizophrenia," *American Journal of Psychiatry* 145(1), 11-18.
Hennekens, C. H. et al. (2005) "Schizophrenia and increased risks of cardiovascular disease," *American Heart Journal* 150(6), 1115-1121.
Hoang, H. H. et al. (2013) "L-arginine, tetrahydrobiopterin, nitric oxide and diabetes," *Current Opinion in Clinical Nutrition and Metabolic Care* 16(1), 76-82.

Karson, C. N. et al. (1996) "Nitric oxide synthase (NOS) in schizophrenia," *Molecular and Chemical Neuropathology* 27(3), 275-284.
Kay, S. R. et al. (1987) "The positive and negative syndrome scale (PANSS) for schizophrenia," *Schizophrenia Bulletin* 13(2), 261-276.
Kelly, D. L. et al. (2015) "Adjunctive Minocycline in Clozapine-Treated Schizophrenia Patients With Persistent Symptoms," *Journal of Clinical Psychopharmacology* 35(4), 374-381,.
Khodaie-Ardakani, M.-R. et al. (2014) "Minocycline add-on to risperidone for treatment of negative symptoms in patients with stable schizophrenia: Randomized double-blind placebo-controlled study," *Psychiatry Research* 215(3), 540-546.
Kirsch, I. et al. (2008) "Initial Severity and Antidepressant Benefits: A Meta-Analysis of Data Submitted to the Food and Drug Administration," *PLoSMedicine* 5(2), e45.
Kirsch, I. et al. (2002) "The emperor's new drugs: An analysis of antidepressant medication data submitted to the U.S. Food and Drug Administration," *Prevention & Treatment* 5(1), No Pagination Specified-No Pagination Specified.
Koga, M. et al. (2016) "Implications for reactive oxygen species in schizophrenia pathogenesis," *Schizophrenia Research* 176(3), 52-71.
Levav, I. et al. (2002) "The WHO World Health Report 2001 new understanding—new hope," *Israeli Journal of Psychiatry and Related Sciences* 39(3), 50-56.
Liu, F. et al. (2014) "Minocycline supplementation for treatment of negative symptoms in early-phase schizophrenia: A double blind, randomized, controlled trial," *Schizophrenia Research* 153(3), 169-176.
Liu, F. et al. (2018) "Changes in plasma levels of nitric oxide metabolites and negative symptoms after 16-week minocycline treatment inpatients with schizophrenia," *Schizophrenia Research* 199, 390-394.
Maia-De-Oliveira, J. et al. (2015) "The Effects of Sodium Nitroprusside Treatment on Cognitive Deficits in Schizophrenia A Pilot Study," *Journal of Clinical Psychopharmacology* 35, 1.
Malaspina, D. et al. (2013) "Schizoaffective Disorder in the DSM-5," *Schizophrenia Research* 150(3), 21-25.
Matosin, N. et al. (2016) "Molecular evidence of synaptic pathology in the CA1 region in schizophrenia," *npj Schizophrenia* 2(3), 16022.
Monte, A. S. et al. (2013) "Prevention and reversal of ketamine-induced schizophrenia related behavior by minocycline in mice: Possible involvement of antioxidant and nitrergic pathways," *Journal of Psychopharmacology* 27(11), 1032-1043.
Narayan, C. L. et al. (2015) "Schizophrenia in identical twins," *Indian journal of psychiatry* 57(3), 323-324.
Nasyrova, R. F. et al. (2015) "Role of nitric oxide and related molecules in schizophrenia pathogenesis: biochemical, genetic and clinical aspects," *Frontiers in Physiology* 6, 139.
Oya, K. et al. (2014) "Efficacy and tolerability of minocycline augmentation therapy in schizophrenia: a systematic review and meta-analysis of randomized controlled trials," *Human Psychopharmacology: Clinical and Experimental* 29(5), 483-491.
Pang, T. et al. (2012) "Minocycline ameliorates LPS-induced inflammation in human monocytes by novel mechanisms including LOX-1, Nur77 and LITAF inhibition," *Biochimica et Biophysica Acta (BBA)—General Subjects* 1820(4), 503-510.
Pi, R. et al. (2004) "Minocycline prevents glutamate-induced apoptosis of cerebellar granule neurons by differential regulation of p38 and Akt pathways," *Journal of Neurochemistry* 91(5), 1219-1230.
Prast, H. et al. (1998) "Nitric Oxide-Induced Release of Acetylcholine in the Nucleus Accumbens: Role of Cyclic GMP, Glutamate, and GABA," *Journal of Neurochemistry* 71(1), 266-273.
Ramirez, J. et al. (2004) "Low concentration of nitrite and nitrate in the cerebrospinal fluid from schizophrenic patients: a pilot study," *Schizophrenia Research* 68(2), 357-361.
Richards. (2014) The Oxford Handbook of Depression and Comorbidity, p. 254, Oxford University Press.
Roe, N. D. et al. (2012) "Nitric oxide synthase uncoupling: A therapeutic target in cardiovascular diseases," *Vascular Pharmacology* 57(5), 168-172.

(56) References Cited

OTHER PUBLICATIONS

Rössler, W. et al. (2005) "Size of burden of schizophrenia and psychotic disorders," *European Neuropsychopharmacology* 15(A), 399-409.
Saeedi Saravi, S. S. et al. (2016) "On the effect of minocycline on the depressive-like behavior of mice repeatedly exposed to malathion: interaction between nitric oxide and cholinergic system," *Metabolic Brain Disease* 31(3), 549-561.
Semple, D. (2005) *Oxford Hand Book of Psychiatry*, Oxford Press.
Shapiro, P. D. (2010) "Chapter 11. Forensic First Response," in *Forensic Nursing Science* (Lynch, V. A., et al., Eds.), p. 453-493, Elsevier Health Sciences.
Shorter, K. R. et al. (2015) "Epigenetic mechanisms in schizophrenia," *Progress in Biophysics and Molecular Biology* 118(1-2), 1-7.
Skelton, M. et al. (2015) "Treatments for delusional disorder," *Cochrane Database of Systematic Reviews*(5), Cd009785.
Socco, S. et al. (2017) "Epigenetics: The third pillar of nitric oxide signaling," *Pharmacological Research* 121, 52-58.
Stern, J. E. (2004) "Nitric oxide and homeostatic control: an intercellular signalling molecule contributing to autonomic and neuroendocrine integration?," *Progress in Biophysics and Molecular Biology* 84(2), 197-215.
Stone, J. M. et al. (2016) "The effect of sodium nitroprusside on psychotic symptoms and spatial working memory in patients with schizophrenia: a randomized, double-blind, placebo-controlled trial," *Psychological Medicine* 46(16), 3443-3450.
Tachikawa, M. et al. (2018) "Developmental changes of l-arginine transport at the blood-brain barrier in rats," *Microvascular Research* 117, 16-21.
Trevlopoulou, A. et al. (2016) "The nitric oxide donor sodium nitroprusside attenuates recognition memory deficits and social withdrawal produced by the NMDA receptor antagonist ketamine and induces anxiolytic-like behaviour in rats," *Psychopharmacology* 233(6), 1045-1054.
Von Bohlen Und Halbach, O. et al. (2002) "Spatial Nitric Oxide Imaging Using 1,2-Diaminoanthraquinone to Investigate the Involvement of Nitric Oxide in Long-Term Potentiation in Rat Brain Slices," *NeuroImage* 15(3), 633-639.
Yamamoto, T. et al. (1993) "Nitric oxide synthase inhibitor blocks spinal sensitization induced by formalin injection into the rat paw," *Anesthesia & Analgesia* 77(5), 886-890.
Zhang, L. et al. (2014) "Profile of minocycline and its potential in the treatment of schizophrenia," *Neuropsychiatric disease and treatment* 10, 1103-1111.
PCT International SearchReport of International Application No. PCT/US2018/053217 dated Dec. 31, 2018.

COMBINATION TREATMENT FOR NEUROPSYCHIATRIC DISORDERS

FIELD OF THE INVENTION

The present invention is related to compositions and methods of treatment for various neuropsychiatric disorders. For example, a composition comprising a combination of metabolic pathway substances and co-factors that regulate the nitric oxide pathway may be useful in treating such neuropsychiatric disorders. In some cases a combination of L-arginine and tetrahydrobiopterin (BH4) may be useful as these compounds both cross the blood brain barrier and interact with the NMDA-NO-cGMP pathway but bypass an impaired NMDA receptor. Such combination compositions are expected to maximize NO's neuroprotection and neuroplasticity effects and minimize NO's neurotoxic effects.

BACKGROUND

Currently available antineuropsychiatric medications all fall into the "me too" category which are directed to regulation of a dopamine D2 receptor. Consequently, no significant progress has been made for new drug development to improve impaired NMDA receptor function in schizophrenia. Such D2 receptor oriented therapy has significant adverse effects, such as extrapyramidal symptoms and cardiometabolic side effects, which require safety monitoring.

What is needed in the art is a compound or compound combination that has a benign safety profile (e.g., for example, nutrient supplements), no need for intensive safety monitoring, no significant cardiometabolic side effects that are associated with currently available antineuropsychiatric medications.

SUMMARY OF THE INVENTION

The present invention is related to compositions and methods of treatment for various neuropsychiatric disorders. For example, a composition comprising a combination of metabolic pathway substrates and co-factors that regulate the nitric oxide pathway may be useful in treating such neuropsychiatric disorders. In some cases a combination of L-arginine and tetrahydrobiopterin (BH4) may be useful as these compounds both cross the blood brain barrier and interact with the NMDA-NO-cGMP pathway but bypass an impaired NMDA receptor. Such combination compositions are expected to maximize NO's neuroprotection and neuroplasticity effects and minimize NO's neurotoxic effects.

In one embodiment, the present invention contemplates a method, comprising: a) providing: i) a patient comprising an uncoupled nitric oxide synthase pathway and exhibiting at least one symptom of a neuropsychiatric disorder: and ii) a pharmaceutical composition comprising L-arginine and tetrahydrobiopterin; b) administering said pharmaceutical composition to said patient under conditions such that said uncoupled nitric oxide synthase pathway converts to a coupled nitric oxide synthase pathway and said at least one symptom of a neuropsychiatric disorder is reduced. In one embodiment, said uncoupled nitric oxide synthase pathway underproduces nitric oxide. In one embodiment, said uncoupled nitric oxide synthase pathway overproduces superoxide, hydrogen peroxide and peroxynitrite. In one embodiment, aid superoxide, hydrogen peroxide and peroxynitrite confers neurotoxicity and induces said at least one symptom of a neuropsychiatric disorder. In one embodiment, said coupled nitric oxide synthase pathway produces a homeostatic level of nitric oxide. In one embodiment, said homeostatic level of nitric oxide confers neuroprotection. In one embodiment, said coupled nitric oxide synthase pathway produces minimal levels of superoxide, hydrogen peroxide and peroxynitrite. In one embodiment, said homeostatic level of nitric oxide confers neuroplasticity. In one embodiment, said neuropsychiatric disorder is schizophrenia. In one embodiment, said neuropsychiatric disorder is depression. In one embodiment, said neuropsychiatric disorder is bipolar disorder. In one embodiment, said neuropsychiatric disorder is delusion. In one embodiment, said neuropsychiatric disorder is selected from the group consisting of schizotypal personality disorder, delusional disorder, brief neuropsychiatric disorder, schizophreniform disorder, schizoaffective disorder, substance/medication-induced neuropsychiatric disorder, neuropsychiatric disorder due to another medical condition, catatonia, depressive disorders and bipolar and related disorders. In one embodiment, said uncoupled nitric acid synthase pathway is an uncoupled endothelial nitric acid synthase pathway. In one embodiment, said administering occurs over a twenty-one-day period.

In one embodiment, the present invention contemplates a pharmaceutical composition comprising L-arginine and tetrahydrobiopterin. In one embodiment, the pharmaceutical composition comprises 6 grams of said L-arginine. In one embodiment, the pharmaceutical composition comprises 500 mg of said tetrahydrobiopterin. In one embodiment, the pharmaceutical composition comprises a liquid. In one embodiment, the pharmaceutical composition comprises a powder. In one embodiment, the pharmaceutical composition comprises a tablet. In one embodiment, the pharmaceutical composition comprises a capsule.

Definitions

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity but also plural entities and also includes the general class of which a specific example may be used for illustration. The terminology herein is used to describe specific embodiments of the invention, but their usage does not delimit the invention, except as outlined in the claims.

The term "about" or "approximately" as used herein, in the context of any assay measurements refers to +/−5% of a given measurement.

The term "uncoupled" as used herein refers to a dysregulation of an enzymatic pathway involving electron transport. For example, electrons in an uncoupled pathway undergo incomplete reactions thereby resulting in the production of oxidized byproducts. In particular, an uncoupled nitric oxide pathway produces oxidized byproducts including but not limited to superoxide, hydrogen peroxide and/or peroxynitrite.

The term "coupled" as used herein refers to a properly regulated enzymatic pathway involving electron transport. For example, electrons in a coupled pathway undergo complete reactions thereby resulting in the production of physiologically compatible products. In particular, a coupled nitric oxide pathway produces nitric oxide at homeostatic levels.

The term "neuropsychiatric disorder" as used herein refers to mental psychosis including but not limited to neuropsychiatric illnesses, psychosis due to general medical conditions, and/or substance-induced psychosis. In particular, a neuropsychiatric disorder may include but is not limited to schizophrenia, depression, bipolar disorder and/or delusions, schizotypal personality disorder, delusional disorder, brief neuropsychiatric disorder, schizophreniform disorder, schizophrenia, schizoaffective disorder, substance/medication-induced neuropsychiatric disorder, neuropsychiatric disorder due to another medical condition, and catatonia. Should we include all these conditions? In addition, should we include "depressive disorders" and "bipolar and related disorders"

The term "converts" as used herein refers to an interaction of a compound with an uncoupled electron transport pathway, where the compound undergoes a chemical transformation that shifts the pathway equilibrium into a coupled electron transport pathway. For example, the addition of tetrahydrobiopterin converts an uncoupled nitric oxide synthase pathway into a coupled nitric oxide synthase pathway by re-establishing the homeostatic tetrahydrobiopterin/dihydrobiopterin ratio within the pathway.

The term "confers" as used herein refers to an interaction of a compound with a neuronal tissue, where the compound undergoes a chemical transformation that either results in neuroprotection or neurotoxicity.

The term "neurotoxicity" as used herein refers to neuronal tissue damage caused by, for example, inflammation or oxidation.

The term "neuroprotection" as used herein refers to the relative preservation of neuronal structure and/or function. In the case of an ongoing insult (e.g., oxidative stress) the relative preservation of neuronal integrity implies a reduction in the rate of neuronal loss over time. Neuroprotection aims to prevent or slow disease progression and secondary injuries by halting or at least slowing the loss of neurons.

The term "homeostatic" as used herein refers to the maintenance of relatively stable internal physiological conditions. Consequently, "a homeostatic level" of a compound would be considered to be within an expected normal range within a specified population of healthy individuals.

The term "underproduces" as used herein refers to the generation of a compound by a biochemical pathway that is sufficiently below homeostatic levels that the lack of the compound results in a symptom of a neuropsychiatric disorder.

The term "overproduces" as used herein refers to the generation of a compound by a biochemical pathway that is sufficiently above homeostatic levels that the excess of the compound results in a symptom of a neuropsychiatric disorder.

The term "effective amount" as used herein, refers to a particular amount of a pharmaceutical composition comprising a therapeutic agent that achieves a clinically beneficial result (i.e., for example, a reduction of symptoms). Toxicity and therapeutic efficacy of such compositions can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index, and it can be expressed as the ratio LD50/ED50. Compounds that exhibit large therapeutic indices are preferred. The data obtained from these cell culture assays and additional animal studies can be used in formulating a range of dosage for human use. The dosage of such compounds lies preferably within a range of circulating concentrations that include the ED50 with little or no toxicity. The dosage varies within this range depending upon the dosage form employed, sensitivity of the patient, and the route of administration.

The term "symptom", as used herein, refers to any subjective or objective evidence of disease or physical disturbance observed by the patient. For example, subjective evidence is usually based upon patient self-reporting and may include, but is not limited to, pain, headache, visual or auditory disturbances, disorganized thoughts, mood fluctuation, nausea and/or vomiting. Alternatively, objective evidence is usually a result of medical testing including, but not limited to, body temperature, complete blood count, lipid panels, thyroid panels, blood pressure, heart rate, electrocardiogram, tissue and/or body imaging scans.

The term "disease" or "medical condition", as used herein, refers to any impairment of the normal state of the living animal or plant body or one of its parts that interrupts or modifies the performance of the vital functions. Typically manifested by distinguishing signs and symptoms, it is usually a response to: i) environmental factors (as malnutrition, industrial hazards, climate, or psychosocial stress); ii) specific infective agents (as worms, bacteria, or viruses); iii) inherent defects of the organism (as genetic anomalies); and/or iv) combinations of these factors.

The terms "reduce," "inhibit," "diminish," "suppress," "decrease," "prevent" and grammatical equivalents (including "lower," "smaller," etc.) when in reference to the expression of any symptom in an untreated subject relative to a treated subject, mean that the quantity and/or magnitude of the symptoms in the treated subject is lower than in the untreated subject by any amount that is recognized as clinically relevant by any medically trained personnel. In one embodiment, the quantity and/or magnitude of the symptoms in the treated subject is at least 10% lower than, at least 25% lower than, at least 50% lower than, at least 75% lower than, and/or at least 90% lower than the quantity and/or magnitude of the symptoms in the untreated subject.

The term "drug" or "compound" as used herein, refers to any pharmacologically active substance capable of being administered which achieves a desired effect. Drugs or compounds can be synthetic or naturally occurring, non-peptide, proteins or peptides, oligonucleotides or nucleotides, polysaccharides or sugars.

The term "administered" or "administering", as used herein, refers to any method of providing a composition to a patient such that the composition has its intended effect on the patient. An exemplary method of administering is by a direct mechanism such as, local tissue administration (i.e., for example, extravascular placement), oral ingestion, transdermal patch, topical, inhalation, suppository etc.

The term "patient" or "subject", as used herein, is a human or animal and need not be hospitalized. For example, out-patients, persons in nursing homes are "patients." A patient may comprise any age of a human or non-human animal and therefore includes both adult and juveniles (i.e., children). It is not intended that the term "patient" connote a need for medical treatment, therefore, a patient may voluntarily or involuntarily be part of experimentation whether clinical or in support of basic science studies.

The term "pharmaceutically" or "pharmacologically acceptable", as used herein, refer to molecular entities and compositions that do not produce adverse, allergic, or other untoward reactions when administered to an animal or a human.

The term, "pharmaceutically acceptable carrier", as used herein, includes any and all solvents, or a dispersion medium including, but not limited to, water, ethanol, polyol (for example, glycerol, propylene glycol, and liquid polyethylene glycol, and the like), suitable mixtures thereof, and vegetable oils, coatings, isotonic and absorption delaying agents, liposome, commercially available cleansers, and the like. Supplementary bioactive ingredients also can be incorporated into such carriers.

DETAILED DESCRIPTION OF THE INVENTION

Figure 1:
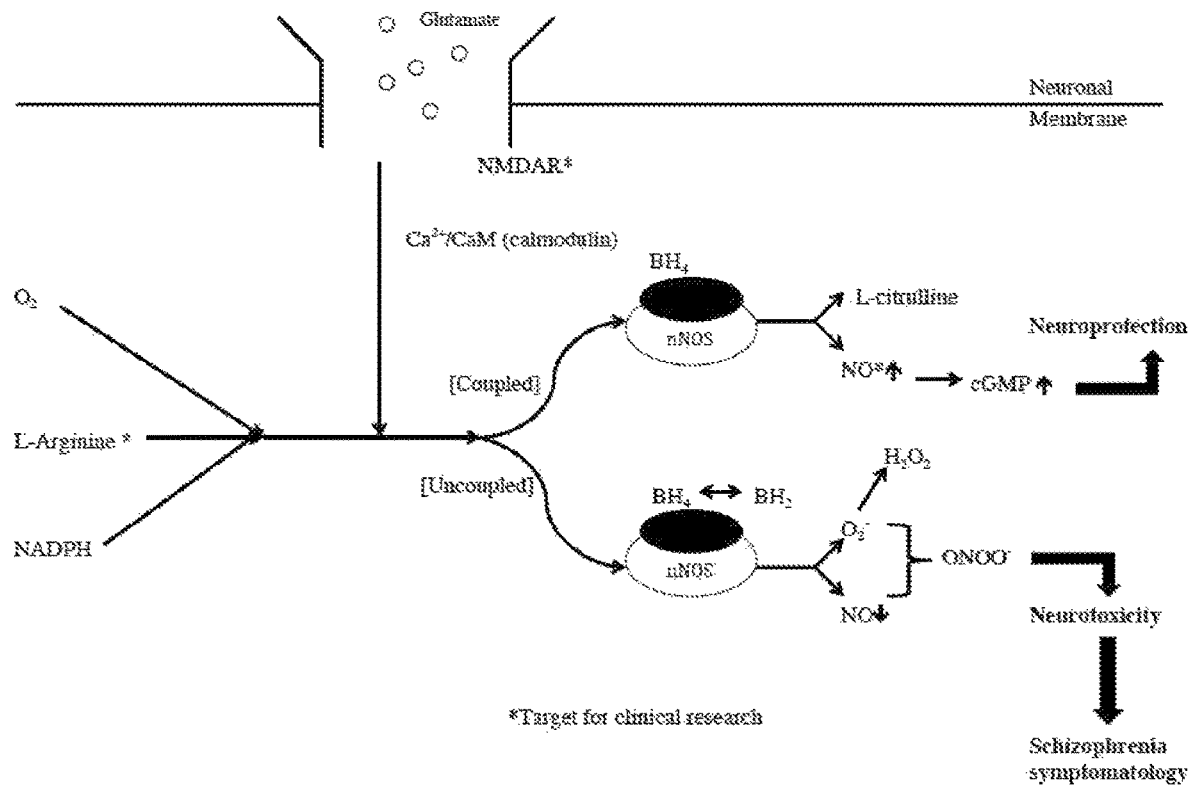
FIG. 1 presents an illustrative nitric oxide synthase (NOS) biochemical pathway that identifies regulatory substrates and cofactors that are able to recouple and uncoupled NOS pathway without producing excess nitric oxide and associated neurotoxicity through the generation of reactive oxygen species (ROS).

The present invention is related to compositions and methods of treatment for various neuropsychiatric disorders. For example, a composition comprising a combination of metabolic pathway substrates and co-factors that regulate the nitric oxide pathway may be useful in treating such neuropsychiatric disorders. In some cases a combination of L-arginine and tetrahydrobiopterin (BH4) may be useful as these compounds both cross the blood brain barrier and interact with the NMDA-NO-cGMP pathway but bypass an impaired NMDA receptor. Such combination compositions are expected to maximize NO's neuroprotection and neuroplasticity effects and minimize NO's neurotoxic effects.

In one embodiment, the present invention contemplates a composition comprising L-arginine and BH4. Although it is not necessary to understand the mechanism of an invention it is believed that L-arginine is a substrate for NOS and has the ability to cross the blood brain barrier. It is further believed that BH4 is a co-factor for NOS and also has the ability to cross the blood brain barrier. When administered to a patient exhibiting at least one symptom of a neuropsychiatric disorder a composition comprising L-arginine and BH4 would be expected to have a synergistic effect that: i) recouples an uncoupled NOS pathway; ii) increases nitric oxide bioavailability; iii) maximizes nitric oxide—induced neuroprotection and neuroplasticity; and iv) minimize nitric oxide—induced oxidative stress, nitrosative stress and associated neurotoxicity.

1. Nitric Oxide Treatment of Neuropsychiatric Disorders

Numerous neuropsychiatric disorders including but not limited to schizophrenia are believed to be a severe, chronic and debilitating mental illnesses. Although currently available antineuropsychiatric medications are effective in reducing positive symptoms, these agents have only limited effect in mitigating negative symptoms and cognitive deficits. One alternative approach has investigated whether nitric oxide (NO) and its metabolites (nitrites and nitrates) may have therapeutic value. Bernstein et al., "The many faces of nitric oxide in schizophrenia. A review." Schizophr. Res. 78:69-86 (2005); Nasyrova et al. "Role of nitric oxide and related molecules in schizophrenia pathogenesis: biochemical genetic and clinical aspects" Front. Physiol. 6:139. (2015). For example, low levels of nitric oxide metabolites in the cerebrospinal fluid have been found in patients with schizophrenia. Ramirez et al., "Low concentration of nitrite and nitrate in the cerebrospinal fluid from schizophrenic patients: a pilot study" Schizophr. Res. 68:357-361 (2004). More recently, studies have reported that a 4-hour intravenous infusion of sodium nitroprusside, a donor of nitric oxide, significantly improved psychopathology and cognitive deficits in patients with schizophrenia. Hallak et al., "Rapid improvement of acute schizophrenia symptoms after intravenous sodium nitroprusside: a randomized, double-blind, placebo-controlled trial" JAMA Psychiatry 70:668-676 (2013); and Maia-de-Oliveira et al. "The effects of sodium nitroprusside treatment on cognitive deficits in schizophrenia: a pilot study" J. Clin. Psychopharmacol. 35:83-85 (2015). However, a more recent study reported negative findings in a separate group of patients with schizophrenia. Stone et al., "The effect of sodium nitroprusside on neuropsychiatric symptoms and spatial working memory in patients with schizophrenia, a randomized, double-blind, placebo-controlled trial" Psychol. Med. 46:3443-3450 (2016).

Generally speaking, it appears that the conventional collective approach indicates that NMDAR hypofunction represents an etiology of schizophrenia by modulating NMDAR's downstream effects via NMDA-NO-cGMP pathway with direct infusion of lipid-soluble NO thereby bypassing the NMDAR pathway and directly elevating intracellular NO levels. In 2013, In particular is the above reported rapid improvement of acute schizophrenia symptoms after a single four-hour-long infusion of 0.5 µg/kg/min intravenous sodium nitroprusside (SNP), a prodrug that releases NO when metabolized. In this randomized, double-blinded, placebo-controlled trial of 20 subjects, significant improvement of positive, negative, anxiety, and depressive symptoms (measured by BPRS-18 and PANSS) was seen in the experimental group, but not in the control group. Such reduction of symptoms was both rapid (some seen within two hours of infusion) and persistent (at least for four weeks after infusion). Hallak et al., "Rapid improvement of acute schizophrenia symptoms after intravenous sodium nitroprusside: a randomized, double-blind, placebo-controlled trial." JAMA Psychiatry 70(7): 668-676 (2013).

A replication study, however, revealed that SNP infusion did not lead to any reduction in schizophrenia symptoms or improvement in cognitive function compared to placebo. Stone et al. (2016). The design of this study was similar to Hallak's: randomized, double-blinded, placebo-controlled trial of 20 subjects, who were reassessed for symptoms and cognitive performance both immediately after the infusion and 4 weeks later. These data attributed the discrepant findings to the fact that the study patients had longer history of schizophrenia and less severe negative symptoms or that SNP may have differential therapeutic effects in schizophrenia patients at different disease stages or different symptom domains. Stone et al., "The effect of sodium nitroprusside on neuropsychiatric symptoms and spatial working memory in patients with schizophrenia: a randomized, double-blind, placebo-controlled trial." Psychol Med 46(16): 3443-3450 (2016). Even though the study samples might not have been strictly comparable in these two clinical trials, the inconsistent data has further compounded a seemingly nebulous role that NO plays in schizophrenia etiology.

Consequently, the obvious drawbacks of direct nitric oxide therapies should be noted. Not only is a four-hour-long IV infusion rather invasive, but also expensive and cumbersome. Accessibility will also be an issue for the patient as direct monitoring at a hospital setting is required. With these apparent limitations and unknown long-term (>4 weeks) therapeutic effects, it is still unknown whether SNP infusion can be an effective treatment option for adult patients with schizophrenia. In addition to these practical concerns, unnecessarily increasing intracellular NO levels by SNP infusion without re-regulating an uncoupled NOS pathway may increase the risk for nitrosative stress, oxidative stress and neurotoxicity. Consequently, it is still unknown whether the direct administration of nitric oxide in neuropsychiatric patients has a therapeutic benefit.

II. Nitric Oxide Metabolic Pathway Regulation Treatment of Neuropsychiatric Disorders Nitric oxide (NO), despite being recognized as a common air pollutant, may also be a chemical agent having various biological functions. For instance, the journal Science selected NO as the "Molecule of the year" in 1992, and American pharmacologists Robert Furchgott, Louis Ignarro, and Ferid Murad were awarded the Nobel Prize in 1998 for their significant contribution in discovering how the ubiquitous production of NO modulates a plethora of bodily actions, including cardiovascular, immune, and nervous system regulation. Calabrese et al., "Nitric oxide in the central nervous system: neuroprotection versus neurotoxicity" *Nat Rev Neurosci* 8:766-775 (2007). NO is a known vasodilator, but can also act as a neurotransmitter mediated by a cGMP-dependent second messenger system which is beloved to play a role in both the central and peripheral nervous systems. Activation of cerebellar NMDA receptors has been reported to lead to the release of NO in the brain. Garthwaite et at., "Endothelium-derived relaxing factor release on activation of NMDA receptors suggests role as intercellular messenger in the brain" *Nature* 336(6197):385-388 (1988). A subsequent report suggests various neuromodulatory effects of NO in the central nervous system. Guix et at., "The physiology and pathophysiology of nitric oxide in the brain" *Prog Neurobiol* 76:126-152 (2005). Other observations suggest that NO: i) stimulates the release of "classical" neurotransmitters such as acetylcholine or GABA (Prast et at., "Nitric oxide-induced release of acetylcholine in the nucleus accumbens: role of cyclic GMP, glutamate, and GABA" *J. Neurochem* 71:266-273 (1998)); ii) is associated with nociceptive transmission in the spinal cord (Yamamoto et at., "Nitric oxide synthase inhibitor blocks spinal sensitization induced by formalin injection into the rat paw" *Anesth Analg* 77:886-890 (1993)); iii) regulates the sleep cycle in the mesencephalon (Hars et al., "Endogenous nitric oxide in the rat pons promotes sleep" *Brain Res* 816:209-219 (1999)); and iv) facilitates synaptic plasticity in the hippocampus (Haley et al., "The role of nitric oxide in hippocampal long-term potentiation" *Neuron* 8:211-216 (1992).

A. Synthesis

NO is released when amino acid L-arginine is converted to L-citrulline by nitric oxide synthase (NOS) with the help of cofactors nicotinamide adenine dinucleotide phosphate (NADPH), flavin mononucleotide (FMN), flavin adenine dinucleotide (FAD), calmodulin, heme, and most importantly, tetrahydrobiopterin (BH4). There are three isoforms of the NOS family, namely neuronal NOS (nNOS, type I), inducible NOS (iNOS, type II), and endothelial NOS (eNOS, type III). Both nNOS and eNOS are Ca2+-calmodulin-dependent enzymes constitutively expressed in mammalian cells, and they tend to synthesize increments of NO that lasts a few minutes. Roe et al., "Nitric oxide synthase uncoupling: a therapeutic target in cardiovascular diseases" *Vascul Pharmacol.* 2012; 57(5-6):168-72. In contrast, iNOS is $Ca^{2+}$-calmodulin-independent, synthesized de novo, and a high-output enzyme that generates high amounts of NO lasting hours to days. Additionally, each isoform is known to regulate different physiological functions: primarily expressed in populations of developing or mature neurons, particularly those of the hypothalamic supraoptic nucleus and paraventricular nucleus, nNOS accounts for about 90% of the total NO production, and plays a role in CNS synaptic plasticity, central regulation of blood pressure, and smooth muscle relaxation; iNOS is mostly found in immune and glial cells and its major functions include induction of inflammatory reactions following infection or trauma, thereby contributing to pathophysiology of inflammatory diseases and septic shock; eNOS, expressed in endothelial cells, is almost exclusively responsible for vascular NO production and confers vasoprotection and anti-atherosclerotic effects. Guix et al., "The physiology and pathophysiology of nitric oxide in the brain" *Prog Neurobiol.* 2005; 76(2):126-52; 16. Stern J E. "Nitric oxide and homeostatic control: an intercellular signalling molecule contributing to autonomic and neuroendocrine integration?" *Prog Biophys Mol Biol.* 2004; 84(2-3): 197-215; and Forstermann et al., "Therapeutic effect of enhancing endothelial nitric oxide synthase (eNOS) expression and preventing eNOS uncoupling" *Br J Pharmacol.* (2011) 164(2):213-223.

B. Pathway Regulation: Coupling Dynamics

One aspect of NO that has been linked to a number of pathological disease states is its association to oxidative stress and ability to generate reactive oxygen species (ROS). NO is a molecule accompanied by 11 valence electrons, 6 of which are from oxygen and 5 from nitrogen. The unpaired 11th electron occupies the last orbital by itself, thereby rendering NO a free radical. For this reason, NO is thermodynamically unstable and can easily react with other reactive species. Guix et at., "The physiology and pathophysiology of nitric oxide in the brain" *Prog Neurobiol* 76:126-152 (2005). In a typical NO production reaction, functional nitric oxide synthase (NOS) transfers electrons from NADPH via FMN and FAD to heme in the amino-terminal oxygenase domain.

When the NOS pathway is carefully regulated (e.g., within homeostatic parameters) the substrate L-arginine is oxidized to L-citrulline and a homeostatic level of NO is produced to carry out its function as a physiological regulator. However, when the tightly controlled flow of electrons within the NOS goes awry (e.g., conventionally referred to as uncoupled) and the chemical reduction of oxygen is disturbed an unwanted generation of ROS including but not limited to, superoxide, hydrogen peroxide and peroxynitrite, may occur. In other words, an uncoupled and/or dysregulated NOS pathway produces superoxide ($O^{2-}$) from the oxygenase domain. Forstermann et al., "Therapeutic effect of enhancing endothelial nitric oxide synthase (eNOS) expression and preventing eNOS uncoupling." *Br J Pharmacol* 164(2):213-223 (2011). To make matters worse, NO itself can react with superoxide, thereby generating an even stronger oxygen radical-peroxynitrite ($ONOO^-$). The majority of ROS in the vasculature is generated by NADPH oxidase (NOX) and endothelial nitric oxidase synthase (eNOS) uncoupling, the latter of which may be strongly association with endothelial dysfunction.

In one embodiment, the present invention contemplates a method for regaining homeostatic control of an uncoupled NOS pathway (e.g., convert to a coupled NOS pathway). Although it is not necessary to understand the mechanism of an invention it is believed that compositions and methods to re-regulate and/or "re-couple" an uncoupled NOS pathway offers new insights into pathogenesis and therapeutic possibilities for endothelial dysfunction. In one embodiment, the re-coupled NOS pathway comprises an eNOS pathway. In one embodiment, the eNOS cofactor BH4 regulates a balance between a coupled eNOS pathway and an uncoupled eNOS pathway. Although it is not necessary to understand the mechanism of an invention, it is believed that BH4 depletion-induced eNOS uncoupling can occur either by oxidation or diminished expression of the recycling enzyme dihydrofolate reductase (DHFR) which results in an overall reduction of available BH4. Roe et al., "Nitric oxide synthase uncoupling: a therapeutic target in cardiovascular diseases" *Vascul Pharmacol* 57:168-172 (2012). First off, it should be noted that BH4 can be synthesized either by a de novo pathway or a salvage pathway. Through a de novo pathway, BH4 is generated from a three-step process from guanosine triphosphate (GTP) to tetrahydrobiopterin (BH4) via the rate-limiting GTP cyclohydrolase (GTPCH), 6-pyruvoyl tetrahydropterin synthase (PTPS) and sepiapterin reductase enzyme. Kietadisorn et at., "Tackling endothelial dysfunction by modulating NOS uncoupling: new insights into its pathogenesis and therapeutic possibilities" *Am J Physiol Endocrinol Metab* 302:E481-495 (2012). In a salvage pathway, oxidized 7,8 dihydrobiopterin is recycled back to BH4 using DHFR. Roe et al., "Nitric oxide synthase uncoupling: a therapeutic target in cardiovascular diseases" *Vascul Pharmacol* 57:168-172 (2012).

When oxidative stress is applied, an uncoupling effect can occur across at least two levels: i) superoxide can directly oxidize BH4 to BH2 thereby destabilizing the NOS dimer thereby reducing the BH4/BH2 ratio; and ii) decreased DHFR expression can lower BH4 availability, thereby reducing the activity of the salvage pathway. When overall BH4 levels become low and inadequate, eNOS becomes unstable and uncoupled leading to reduced NO production and elevated superoxide generation. Left unchecked, the remaining NO and newly generated superoxide molecules interact to form peroxynitrite, a potent oxidant, which further oxidizes BH4 and the viscous cycle continues.

In one embodiment, the present invention contemplates a method comprising treating a neuropsychiatric disorder pathophysiology by recoupling an uncoupled NOS pathway. In one embodiment, the uncoupled NOS pathway results in an underproduction of NO. In one embodiment, the uncoupled NOS pathway results in ROS interacting with available NO.

Although it is not necessary to understand the mechanism of an invention it is believed that an underproduction of NO may result in a neuropsychiatric disorder mediated by its role as a second messenger of N-methyl-D-aspartate receptor (NMDAR) activation, which interacts with both dopaminergic and serotonergic pathways. Bitanihirwe et al., "Oxidative stress in schizophrenia: an integrated approach" *Neurosci Biobehav Rev* 35:878-893 (2011). It is further believed that when glutamate binds to NMDAR it generates long excitatory post-synaptic currents that are specifically important for generating spike bursts in the hippocampus and ventral tegmental area. NMDAR channels are permeable to $Ca^{2+}$, this $Ca^{2+}$ flux through the NMDAR-gated channels binds to calmodulin and stimulates the NOS enzyme to produce NO in the nervous system NO subsequently activates guanylate cyclase, which increases the production of cyclic GMP (cGMP). This NMDA-NO-cGMP pathway is thought to modulate the release of neurotransmitters such as glutamate and has been regarded to be involved in the refinement and/or maintenance of synaptic connections, including synaptic long-term potentiation induction and cellular correlates of memory. Cohen et al., "The impact of NMDA receptor hypofunction on GABAergic neurons in the pathophysiology of schizophrenia" *Schizophr Res* 167:98-107 (2015). Overall, a pathological state of NMDAR hypofunction may lead to an underproduction of NO where aspects of normal brain function are hampered such that schizophrenia symptomatology can arise.

While properly regulated NO production is believed to confer neuroprotection, when NO is overproduced under particular circumstances such as oxidative stress or lack of cofactors, NOS can undergo uncoupling and produce reactive oxygen species (ROS) that interacts with available NO and produces more NOS, thereby conferring neurotoxicity. Although it is not necessary to understand the mechanism of an invention, it is believed that the uncoupled NOS generated ROS may confer neuronal neurotoxicity and/or dysfunction by: i) direct damage via inflammation activation; ii) aberrant glutamate neurotransmission; iii) demyelination; and iv) NMDAR hypofunction. It has been reported that ROS can instigate impaired neurodevelopmental processes that underlie schizophrenia. Koga et al., "Implications for reactive oxygen species in schizophrenia pathogenesis" *Schizophr Res* 176:52-71 (2016). Therefore, not only can the downstream effects of NO underproduction induce neurotoxic effects responsible for neuropsychiatric disorders, but so can the by-products of NO overproduction via an uncoupled regulation of NOS. Therefore, NO's "double identity" (neuroprotection versus neurotoxicity) can be reconciled by a balance between the NO-cGMP pathway and NOS uncoupling/nitrosative stress. See, FIG. 1.

Modulation of the NOS pathway, as opposed to direct administration of NO (e.g., nitroprusside treatment), in the treatment of schizophrenia has been attempted using the antibiotic, minocycline. Studies have shown that tetracyclines including minocycline inhibit the expression of NO synthase. Amin et al., "A novel mechanism of action of tetracyclines: effects on nitric oxide synthases" *Proc. Natl. Acad. Sci. U.S.A* 93:14014-14019 (1996); and Amin et al., "Post-transcriptional regulation of inducible nitric oxide synthase mRNA in murine macrophages by doxycycline and chemically modified tetracyclines" *FEBS Lett.* 410:259-264 (1997). In a mouse animal model of depression, it was found that minocycline attenuated depressive-like behavior and decreased hippocampal nitrite level. Saeedi Saravi et al., "On the effect of minocycline on the depressive-like behavior of mice repeatedly exposed to malathion: interaction between nitric oxide and cholinergic system" *Metab. Brain Dis.* 31:549-561 (2016). However, it is unclear whether minocycline might affect NO and its metabolites in patients with schizophrenia, and if yes, whether NO might play a role in moderating or mediating therapeutic response of minocycline in treating schizophrenia.

Minocycline is a semi-synthetic second-generation tetracycline with antimicrobial and anti-inflammatory effects. It has a high oral bioavailability, excellent penetration to the brain, and is well tolerated in humans. Oya et al., "Efficacy and tolerability of minocycline augmentation therapy in schizophrenia: a systematic review and meta-analysis of randomized controlled trials" *Hum Psychopharmacol* 29:483-491 (2014); and Zhang et al., "Profile of minocycline and its potential in the treatment of schizophrenia" *Neuropsychiatr. Dis. Treat.* 10:1103-1111 (2014). Recent clinical studies have suggested that minocycline may help improve schizophrenia symptoms, in particular negative symptoms. Chaudhry et al., "Minocycline benefits negative symptoms in early schizophrenia: a randomised double-blind placebo-controlled clinical trial in patients on standard treatment" *J. Psychopharm.* 26:1185-1193 (2012); Ghanizadeh et al., "Minocycline as add-on treatment decreases the negative symptoms of schizophrenia; a randomized placebo-controlled clinical trial" *Recent Patents On Inflammation & Allergy Drug Discovery* 8: 211-215 (2014); Kelly et al., "Adjunctive Minocycline in Clozapine-Treated Schizophrenia Patients With Persistent Symptoms. *J. Clin. Psychopharmacol.* 35: 374-381 (2015); and Khodaie-Ardakani et al., "Minocycline add-on to risperidone for treatment of negative symptoms in patients with stable schizophrenia: randomized double-blind placebo-controlled study" *Psychiatry Res.* 215: 540-546 (2014) and Liu et al., "Minocycline supplementation for treatment of negative symptoms in early-phase schizophrenia: a double blind, randomized, controlled trial" *Schizophr. Res.* 153:169-176 (2014). However, the mechanisms by which minocycline exerts its beneficial effect in schizophrenia remain unclear.

In a clinical study performed in accordance with Example 1 the results demonstrate that the beneficial effect of adjunctive minocycline treatment on negative neuropsychiatric symptoms are through mechanisms other than the nitric oxide pathway. A total of 79 schizophrenia patients were screened, and 63 were enrolled in this study. Fifty-five patients completed week-16 assessments. Among these 55 completers, 27 were in the minocycline group, 28 in the placebo group. The minocycline group had a significantly shorter disease duration than the placebo group (Mean±SD, 19.0±12.3 versus 30.2±14.5 months, p=0.003). There were no significant differences between the two groups in age, gender, education level, family history of mental illness, BMI and the daily dosage of risperidone received (p's>0.2).

After controlling for baseline values and disease duration, the ANCOVA analysis showed that the minocycline group had significant decreases, compared to the placebo group, in the SANS total sore (−31.2±25.5 versus −25.3±12.8, p<0.001), the PANSS total score (−32.9±17.1 versus −25.3±12.8, p=0.006) and the PANSS negative symptoms score (−10.8±5.9 versus −6.2±4.2, p<0.001) at week 16. In addition, the minocycline group had a significant decrease in plasma levels of NO metabolites (−8.19±18.09 versus 4.37±15.53 μmol/l, p=0.020), but not in plasma levels of IL-1β or TNF-α (p's>0.1), compared to the placebo group. See, Table 1.

TABLE 1

Changes in outcome measures over a sixteen week minocycline administration.

| | Minocycline (N = 27) | | | | Placebo (N = 28) | | | | |
| | Baseline | | Week 16 change | | Baseline | | Week 16 change | | |
| Variable | Mean | SD | Mean | SD | Mean | SD | Mean | SD | P |
| SANS total score | 61.3 | 14.9 | −31.2 | 25.5 | 63.2 | 13.6 | −14.8 | 20.2 | <0.001 |
| PANSS | | | | | | | | | |
| Totaol score | 82.7 | 13.6 | −32.9 | 17.1 | 83.4 | 10.7 | −25.3 | 12.8 | 0.006 |
| Positive symptom score | 17.2 | 5.1 | −8.5 | 5.1 | 16.1 | 4.9 | −7.5 | 4.7 | 0.978 |
| Negative symptom score | 25.0 | 3.1 | −10.8 | 5.9 | 26.3 | 4.3 | −6.2 | 4.2 | <0.001 |
| General psychopathology score | 41.2 | 9.7 | −14.5 | 9.9 | 41.3 | 6.7 | −11.8 | 8.1 | 0.087 |
| BMI (kg/m$^2$) | 21.70 | 2.62 | 1.98 | 1.84 | 22.07 | 3.20 | 1.86 | 1.60 | 0.445 |
| Nitric oxide (μmol/l) | 46.54 | 13.76 | −8.19 | 18.09 | 43.96 | 17.43 | 4.37 | 15.53 | 0.004 |
| IL-1β (pg/ml) | 1.75 | .21 | −0.99 | .25 | 1.76 | 0.20 | −0.08 | 0.24 | 0.180 |
| TNF-α (pg/ml) | 8.08 | 2.21 | −0.97 | 1.76 | 8.62 | 2.51 | −0.97 | 1.77 | 0.320 |

Note:
1) Week 16 change equals week 16 value minus baseline value;
2) BMI body mass index; TNF-α: tissue necrom factor α;
3) P value were based on ANCOVA company between groups differences in week 16 changes controlling for baseline values and disease duration.

Figure 2:
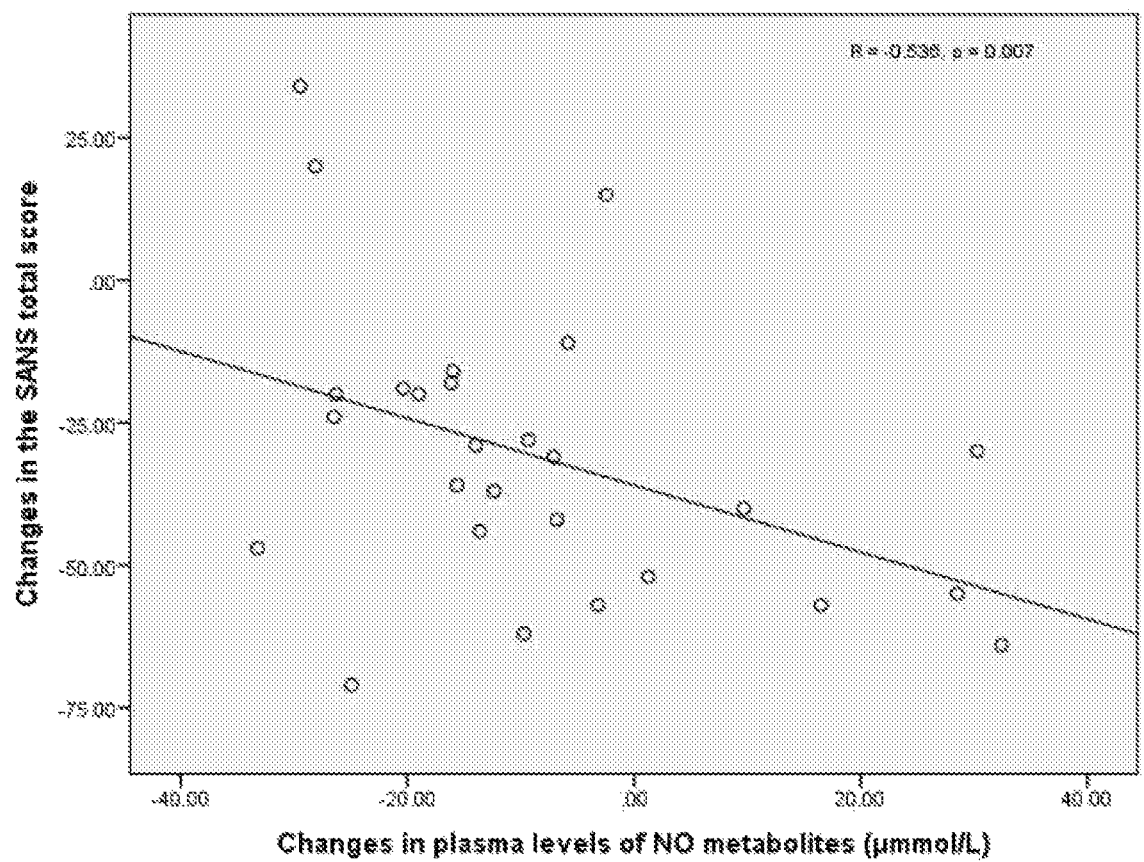
FIG. 2 presents exemplary data showing the therapeutic effect of a sixteen-week minocycline administration in relation to nitric oxide plasma levels in patients having schizophrenia.

Partial correlation analysis was then performed within the minocycline group to examine the relationship between changes in plasma levels of NO metabolites and changes in the SANS total score after 16-week minocycline treatment, controlling for baseline age, disease duration, and BMI. The results showed that the more decrease in plasma levels of nitric oxide metabolites was associated with less improvement in negative symptoms (r=−0.536, p=0.007). See, FIG. 2.

As reported previously, 16-week adjunctive minocycline significantly improved schizophrenia symptoms, in particular the negative symptoms. Liu et al., "Minocycline supplementation for treatment of negative symptoms in early-phase schizophrenia: a double blind, randomized, controlled trial" *Schizophr. Res.* 153:169-176 (2014). In addition, the data presented herein found a significant decrease in plasma levels of NO metabolites at week 16, which seems to counteract the improvement in negative symptoms associated with minocycline treatment.

As discussed above, the NMDA-NO-cGMP pathway is thought to modulate the release of neurotransmitters such as glutamate and dopamine, both of which play a critical role in the etiology and clinical manifestation of schizophrenia. Caravaggio et al., "The effect of striatal dopamine depletion on striatal and cortical glutamate: A mini-review" *Prog. Neuropsychopharmacol. Biol. Psychiatry* 65:49-53 (2016). Therefore, minocycline associated a decrease in NO may counteract the beneficial effect of minocycline treatment in improving negative symptoms, which might be through mechanisms other than the NO signaling pathway.

The underlying mechanisms for minocycline to exert its beneficial effect in improving schizophrenia symptoms remain elusive. A number of studies have suggested that minocycline may have direct modulating effect to NMDA receptor. Specifically, it has been reported that minocycline affects the NMDA receptor signaling by differential regulation of p38 and Akt pathways. Pi et al., "Minocycline prevents glutamate-induced apoptosis of cerebellar granule neurons by differential regulation of p38 and Akt pathways" *J. Neurochem.* 91:1219-1230 (2004). A widely used animal model of schizophrenia involves the acute or repeated administration of ketamine, which is a noncompetitive antagonist to the NMDA receptor. A previous study reported that minocycline was capable of preventing and reversing the behavioral changes in ketamine treated mice. Monte et al., "Prevention and reversal of ketamine-induced schizophrenia related behavior by minocycline in mice: Possible involvement of antioxidant and nitrergic pathways" *J Psychopharm.* 27:1032-1043 (2013).

It has been well established that minocycline exhibits anti-inflammatory and anti-apoptotic properties independent of its antibiotic activity. Garrido-Mesa et al., "What is behind the non-antibiotic properties of minocycline?" *Pharmacol. Res.* 67:18-30 (2013). It was also reported that minocycline significantly reduced the inflammatory response in lipopolysaccharide (LPS)-challenged human monocytes, decreasing LPS-induced transcription of pro-inflammatory TNF-α, IL-1β, interleukin-6 (IL-6) and cyclooxygenase-2 (COX-2), and the LPS-stimulated TNF-α, IL-6 release. Pang et al., "Minocycline ameliorates LPS-induced inflammation in human monocytes by novel mechanisms including LOX-1, Nur77 and LITAF inhibition" *Biochim. Biophys. Acta* 1820: 503-510 (2012).

C. Nitric Oxide Synthase (NOS) Uncoupling

One notable aspect of NO that has been linked to a number of disease states is its association to oxidative stress and ability to generate reactive oxygen species (ROS). NO is a molecule accompanied by 11 valence electrons, 6 of which are from oxygen and 5 from nitrogen. The unpaired 11$^{th}$ electron occupies the last orbital by itself, thereby rendering NO as a free radical. For this reason, NO is thermodynamically unstable and can easily react with other reactive species. Guix et al., "The physiology and pathophysiology of nitric oxide in the brain" *Prog Neurobiol.* (2005) 76(2):126-152.

In a typical NO production reaction, functional NOS transfers electrons from NADPH via FMN and FAD to heme in the amino-terminal oxygenase domain. Through this pathway, the substrate L-arginine is oxidized to L-citrulline, and NO is produced. NO can then carry out its function as a physiological regulator. But due to its aforementioned molecular structure, it can also augment the unwanted generation of ROS. In other words, when the tightly controlled flow of electrons within the NOS goes awry, chemical reduction of oxygen is disturbed. As a consequence, the NO generation pathway becomes uncoupled, and $O_2$ is produced from the oxygenase domain. A further complication is that NO can react with $O_2$ generating an even stronger oxygen radical ONOO$^-$. The majority of ROS in the vasculature is generated by NADPH oxidase (NOX) and eNOS uncoupling, and the latter mechanism has been extensively studied due to its strong association with endothelial dysfunction. Modulation of eNOS uncoupling has offered new insights into pathogenesis and therapeutic possibilities for endothelial dysfunction. Given the biochemical similarities between eNOS and nNOS, it is likely that nNOS may share a similar uoupling process as seen in eNOS. Forstermann et al., "Therapeutic effect of enhancing endothelial nitric oxide synthase (eNOS) expression and preventing eNOS uncoupling" *Br J Pharmacol.* (2011) 164(2):213-223.

D. Tetrahydrobiopterin Interactions

As discussed herein, NO's seemingly contradictory role in neuroprotection and neurotoxicity might be reconciled by the balance of coupling and uncoupling of nitric oxide synthase (NOS). The crux of NO's ability to confer neuroprotection and therapeutic benefit for schizophrenia likely lies on the integrity of NOS in a coupled state.

6R-5,6,7,8-tetrahydrobiopterin (BH4) is a cofactor that supports the biological functioning of all NOS isoforms. Although it is not necessary to understand the mechanisms of an invention, it is believed that BH4 facilitates NADPH-derived electron transfer from NOS reductase to the oxygenase domain in converting L-arginine to N O and L-citrulline. Hoang et al., "L-arginine, tetrahydrobiopterin, nitric oxide and diabetes" *Curr Opin Clin Nutr Metab Care* (2013) 16(1):76-82. When the tight regulation of BH4 goes awry either by BH4 oxidation or diminished expression of the recycling enzyme dihydrofolate reductase (DHFR), the NOS uncoupled state is induced. BH4 is synthesized via de novo or salvage pathway. Roe et al., "Nitric oxide synthase uncoupling: a therapeutic target in cardiovascular diseases" *Vascul Pharmacol.* (2012) 57(5-6):168-172.

Through the de novo pathway, BH4 is generated from a three-step process from guanasine triphosphate (GTP) to tetrahydrobiopterin via the rate-limiting GTP cyclohydrolase (GTPCH), 6-pyruvoyl tetrahydropterin synthase (PTPS) and sepiapterin reductase enzyme. Kietadisorn et al., "Tackling endothelial dysfunction by modulating NOS uncoupling: new insights into its pathogenesis and therapeutic possibilities" *Am J Physiol Endocrinol Metab.* (2012) 302(5):E481-495. While in the salvage pathway, the oxidized 7,8 dihydrobiopterin is recycled back to BH4 using DHFR. Roe et al., "Nitric oxide synthase uncoupling: a therapeutic target in cardiovascular diseases" *Vascul Pharmacol.* (2012) 57(5-6): 168-172.

When oxidative stress occurs, its effect on uncoupling can ensue across two levels: $O_2$ can directly oxidize BH4 to BH2, destabilizing the NOS dimer (represented by low BH4/BH2 ratio and succeeding NOS uncoupling), and decreased DHFR expression can lower BH4 availability, reducing the activity of the salvage pathway. When the overall BH4 level falls short, eNOS becomes unstable and "uncoupled," leading to a subsequently lower NO production and greater $O_2^-$ generation. Eventually, the remaining NO and newly generated $O_2^-$ molecules will interact further to form ONOO$^-$, a potent oxidant, which further oxidizes BH4, and the viscous cycle continues.

Increasing intracellular NO levels alone via intravenous infusion of SNP without regulating the uncoupled NOS may in turn induce greater nitrosative stress, oxidative stress, and neurotoxicity. When more NO is introduced to encounter pre-existing ROS but without the proper form of BH4, uncontrolled interaction between NO and $O_2^-$ may lead to the formation of ONOO$^-$, a compound that will further exacerbate the degree of oxidative and nitrosative stress in the brain.

The solution therefore seems to be twofold: to not only increase the level of NO, but also secure the NOS in its coupled form. Because L-arginine, a substrate for NOS, and BH4, its co-factor, are able to freely cross the BBB, it is likely that the combination of the two compounds would effectively: 1) recouple an uncoupled NOS pathway; 2) increase NO bioavailability; 3) increase NO interaction with the NMDAR-NO-cGMP pathway, bypassing an impaired NMDA receptor; 4) maximize NO induced neuroprotection and neuroplasticity; and 5) minimize NOS uncoupling associated oxidative stress, nitrosative stress and neurotoxicity.

Figure 4:
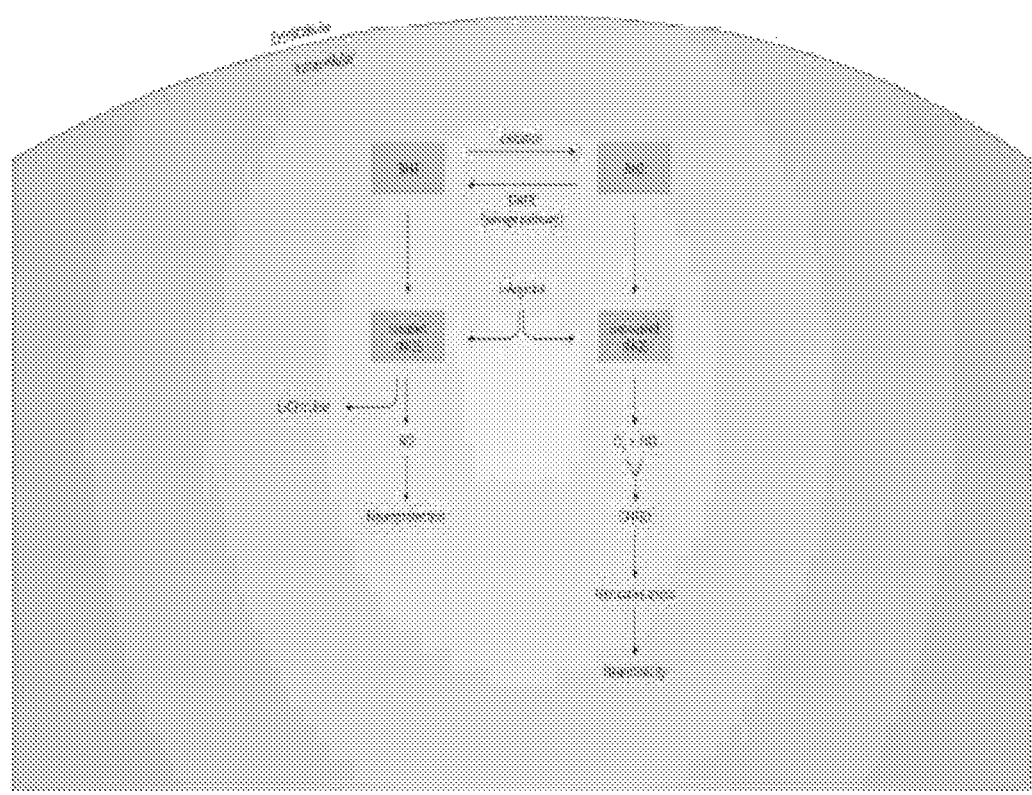
FIG. 4 illustrates a potential role for BH4 in NOS coupling and uncoupling.

Frye et al., "Tetrahydrobiopterin as a novel therapeutic intervention for autism" Neurotherapeutics (2010) 7(3):241-249; Tachikawa et al., "Developmental changes of I-arginine transport at the blood-brain barrier in rats" *Microvasc Res.* (2017) 117:16-21; and FIG. 4.

The data presented herein suggests that NO's role as a neurotransmitter in the NMDAR-NO-cGMP pathway in the CNS has shone light on the pathophysiological process behind schizophrenia. Supporting these data are direct imaging findings, such as diamine 1,2-diamineanothraquinone (a molecule that reacts with NO to form a fluorescent complex)-induced fluorescence in the hippocampal area CA1, a brain area reported to show synaptic pathology in schizophrenia, reveals a promising road to NO related therapeutics for this devastating neuropsychiatric condition. von Bohlen et al., "Spatial nitric oxide imaging using 1,2-diaminoanthraquinone to investigate the involvement of nitric oxide in long-term potentiation in rat brain slices" *Neuroimage* (2002) 15(3):633-639; and Matosin et al., "Molecular evidence of synaptic pathology in the CA1 region in schizophrenia" *NPJ Schizophr.* (2016) 2:16022.

In one embodiment, the present invention contemplates that NO may exert its neuroprotection and therapeutic benefit for schizophrenia by maintaining the integrity of NOS in a coupled state.

E. Epigenetics

In addition to interacting with sGC, NO has been found to directly and indirectly regulate epigenetic protein expression, thereby inducing heritable non-DNA gene modification. Socco et al., "Epigenetics: The third pillar of nitric oxide signaling" *Pharmacol Res.* (2017) 121:52-58. Current data on NO's endogenous epigenetic modulation suggest a hypothesis including, but not limited to, DNA methylation, histone modification, and microRNA (miRNA). The exact mechanism by which NO modulates these three markers have not been fully elucidated, but the effect of NO on transcriptional response seem to be target-dependent. Findings from previous studies regarding NO's role in epigenetic modulation is summarized in Table 2.

Figure 3:
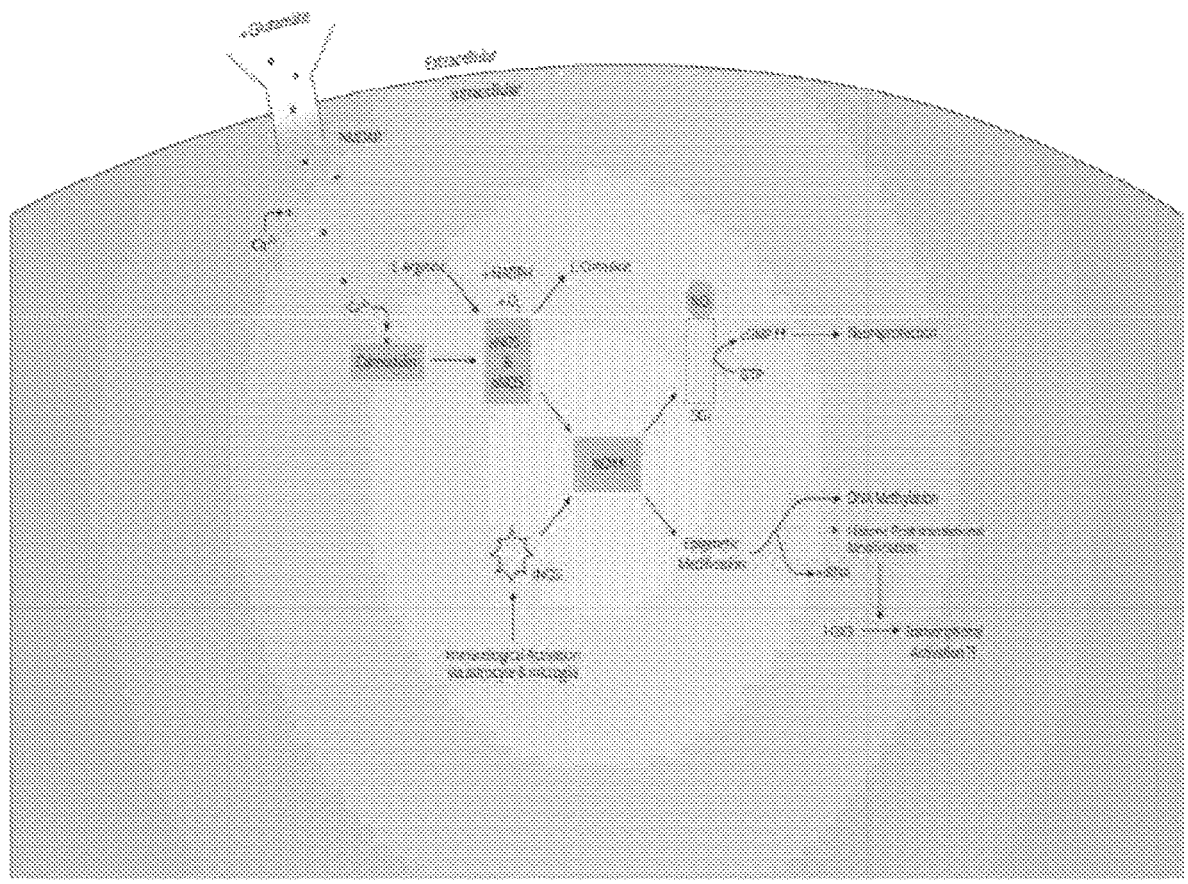
FIG. 3 illustrates a potential epigenetic role involving NO in the expression of schizophrenia.

57(3):323-324; and Cardno et al., "Heritability estimates for psychotic disorders: the Maudsley twin psychosis series" *Arch Gen Psychiatry* (1999) 56(2):162-168. Given the high heritability that is almost twice of the concordance rate, non-DNA heritance and environmental factors contributing to the development of schizophrenia are likely, in turn alluding that epigenetics could be at play. Current literature on epigenetic gene modulation by NO in schizophrenia is sparse. Yet an interesting, albeit limited, point of convergence exists between epigenetic markers directly regulated by NO exposure and epigenetic signaling in schizophrenia. H3K9 is a site of histone post-translational modification. An increase in NO-mediated H3K9 acetylation was reported in both oral squamous cell carcinoma (SCC) patient samples and muscle biopsies of Duchenne muscular dystrophy (DMD) patients. Interestingly enough, histone 3 (H3) is particularly dysregulated in schizophrenia, and di- and tri-methylation of H3K9 has been reported to be specifically elevated in cortical neuronal and adjacent non-neuronal cells in post-mortem tissue studies. Akbarian S., "The molecular pathology of schizophrenia—focus on histone and DNA modifications" *Brain Res Bull* (2010) 83(3-4):103-107. An increase in heterochromatin to euchromatin ratio has also been found in lymphocyte samples of schizophrenia patients, most likely due to increased H3K9 methylation and reduced H3K9 acetylation. Chase et al., "Histone methylation at H3K9: evidence for a restrictive epigenome in schizophrenia" *Schizophr Res.* (2013) 149(1-3): 15-20; and Shorter et al., "Epigenetic mechanisms in schizophrenia" *Prog Biophys Mol. Biol.* (2015) 118(1-2):1-7. Caution must be exercised in interpreting these results given that NO-mediated acetylation of H3K9 was studied in oral mucosa and muscle, not the brain. For example, the role of NO in neuroprotection and epigenetic modulation in patients with schizophrenia may involved both NO synthesis and/or the NMDAR-NO-cGMP signaling pathway. See, FIG. 3.

Given its vast physiological effects, NO has been linked to various neurodegenerative diseases, and so to schizophrenia. Unfortunately, inconsistent findings in the literature on

TABLE 2

Nitric Oxide (NO)-mediated epigenetic modulation

| Target | Mechanism | Finding |
| --- | --- | --- |
| DNA methylation (42, 62-64)) | Transfer of methyl group to the C-5 position of the cytosine ring of DNA by DNA methyltransferase (DNMT) 5-methyl(5-mC) modification of the CpG island in or near promotor region, repression of gene transcription | NO-induced globed decrease in DNA methylation (i.e. 5-mC) NO-Mediated gene silencing effects via DNA methylation NO-Mediated epigentic silencing of tumor suppressor gene in Hellcobactor pylorl |
| Histone post-translational modification (PTM) (65-68) | Site of PTM: amino-terminal tail (e.g. lysine or arginine) on core histone molecule protruding outward from the center of nuleosome Histone acetylation: associated with transcriptional activation Histone methylation: associated with transcriptional activation and inactivation | NO production correlated with hyper-acylation of H3 in oral squamous cell carcinoma (SCC) Cellular differentiation and memory programs impacted by altered acetylation at H3 and H4 Differentiation in embryonic stem cells and cardiomyocytes increased by H3K9me3 activity |
| MicroRNA (mRNA) (68-71) | "Master regulation" of gene expression 18 to 22-nucleotide-long, single-stranded molecule that regulates apoptosis, proliferation, differentiation and metastasis | miR-17, miR-146a, miR-128, miR-223 and miR-221 associated with inducible nitric oxide synthases (INOS) in inflammatory bowel disease (IBD) miR-21associated with INOS in KRAS-induced lung cancer miR-21associated with INOS in ulcerative colitis, Chron's disease, and colon adenomas Up-regulation of 45 miRNA and down-regulation of 72 miRNA associated with NO in triple negative breast cancer cells |

Schizophrenia has a concordance rate of approximately 40% and a heritability of 82-85%. Narayan et al., "Schizophrenia in identical twins" *Indian J Psychiatry* (2015)

the role of NO in schizophrenia attests to an incomplete resolution to the puzzle. For instance, elevated levels of nNOS in the cerebellar vermis, increased numbers of NOS immuno-reactive Purkinje cells and dentate nucleus neurons, and higher levels of nNOS mRNA in the prefrontal cortex have been documented in patients with schizophrenia. Karson et al., "Nitric oxide synthase (NOS) in schizophrenia: increases in cerebellar vermis" *Mol Chem Neuropathol*. (1996) 27(3):275-284; Bernstein et al., "Increased number of nitric oxide synthase immunoreactive Purkinje cells and dentate nucleus neurons in schizophrenia" *J Neurocytol*. (2001) 30(8):661-670; and Baba et al., "Expression of nNOS and soluble guanylate cyclase in schizophrenic brain" *Neuroreport*. (2004) 15(4):677-680. On the other hand, studies have reported that there were no significant differences in the levels of NOS expression in cerebellar granule cells or nN OS protein content in the cerebral cortex between schizophrenia patients and healthy controls. Doyle et al., "Application of [3H]L-N(G)-nitro-arginine labelling to measure cerebellar nitric oxide synthase in patients with schizophrenia" *Neurosci Lett*. (1995) 202(1-2):49-52. In addition, other studies have found decreased activities of nNOS, or NO-sensitive receptors, such as alpha 7 nicotinic acetylcholine receptor, in the cortex of patients with schizophrenia. Freedman et al., "The alpha7-nicotinic acetylcholine receptor and the pathology of hippocampal interneurons in schizophrenia" *J Chem Neuroanat*. (2000) 20(3-4):299-306. A recent study from our group found a significant improvement in negative symptoms and a significant decrease in plasma levels of NO metabolites after 16-week minocycline treatment in patients with schizophrenia; further, a greater decrease in plasma levels of NO metabolites was associated with less improvement in negative symptoms. Liu et al., "Changes in plasma levels of nitric oxide metabolites and negative symptoms after 16-week minocycline treatment in patients with schizophrenia" *Schizophr. Res*. (2018). Such discrepancy in data in fact extends to measures on the levels of NO metabolites in cerebral spinal fluid (CSF) as well. Bernstein et al., "The many faces of nitric oxide in schizophrenia. A review" *Schizophr Res*. (2005) 78(1):69-86.

The seemingly conflicting findings of NO underproduction and overproduction in schizophrenia might be able to reconcile in the context of NOS uncoupling. First, the underproduction of NO in schizophrenia can easily be elucidated by its integral role as a second messenger of NMDAR activation, which interacts with both dopaminergic and serotonergic pathways. Bitanihirwe et al., "Oxidative stress in schizophrenia: an integrated approach" *Neurosci Biobehav Rev*. (2011) 35(3):878-893. NMDA hypofunction in schizophrenia, as described earlier, leads to reduced NO production, whose downstream effects are considered to be related to the manifestation of schizophrenia symptoms.

The case of NO overproduction in schizophrenia does not seem so straightforward considering NO's favorable role in neuroprotection. Nonetheless, under pro-oxidant circumstances, such as oxidative stress or lack of cofactors, NOS can undergo uncoupling and produce ROS; available NO reacts with $O_2^-$ and produces highly neurotoxic $ONOO^-$. Whether it be through direct damage via inflammation activation, aberrant glutamate neurotransmission, demyelination, and again, hypo-function of NMDAR, ROS can instigate impaired neurodevelopmental processes that underlie schizophrenia. Koga et al., "Implications for reactive oxygen species in schizophrenia pathogenesis" *Schizophr Res*. (2016) 176(1):52-71.

Therefore, not only can the downstream effects of NO underproduction induce neurotoxic effects responsible for schizophrenia, but so can the byproducts of NO overproduction via deviant regulation of NOS. While NO itself is neuroprotective, it may lead to neurotoxic effect in the context of oxidative stress and NOS uncoupling.

III. Neuropsychiatric Disorders

Neuropsychiatric disorders are classified within the Diagnostic Statistical Manual V-TR as neuropsychiatric illnesses, psychosis due to general medical conditions, and substance-induced psychosis.

A. Schizophrenia

Ranked among the top ten illness contributing to the global burden of disease and as the 8th leading cause of disability-adjusted-life-years (DALYs), schizophrenia is a multi-factorial syndrome that affects more than 21 million people worldwide. Rossler et al., ""Size of burden of schizophrenia and neuropsychiatric disorders" *Eur Neuropsychopharmacol* 15(4):399-409 (2005); and Levav et al., "The WHO World Health Report 2001 new understanding—new hope" *Isr J Psychiatry Relat Sci* 39(1):50-56 (2002). Clinically, schizophrenia is characterized by thought disturbance, abnormal perception, and impaired cognition, and is often accompanied by various physical manifestations such as motoric neurological soft signs, catatonia, and metabolic disturbances. Bernstein et al., ""Increased number of nitric oxide synthase immunoreactive Purkinje cells and dentate nucleus neurons in schizophrenia." *J Neurocytol* 30(8):661-670 (2005); Heinrichs et al., "Significance and meaning of neurological signs in schizophrenia." *Am J Psychiatry* 145 (1): 11-18 (1988); and Hennekens et al., "Schizophrenia and increased risks of cardiovascular disease." *Am Heart J* 150(6): 1115-1121 (2005).

Despite much progress over the past 100 years since Swiss psychiatrist Eugen Bleuler first coined the term schizophrenia in 1911, our current understanding of etiology behind this mental condition remains unsatisfactory and outcomes dismal: exact cause of schizophrenia is still unknown, and 30% of those under optimal pharmacological therapy remain actively ill, leading to treatment-refractory schizophrenia (TRS). Caspi et al., "Treatment-refractory schizophrenia" *Dialogues Clin Neurosci* 6(1): 61-70 (2004).

As the current diagnosis for schizophrenia is merely based on the clinical presence of three categories of symptoms (positive, negative, and cognitive) without any indicative laboratory tests, much effort has been devoted to identifying a schizophrenia-specific biomarker that would help in early diagnosis and contribute to better understanding of its pathogenesis. The ideal biologic indicator for schizophrenia has not been identified, but one of its strongest candidates is nitric oxide (NO). In fact, with the rise of NMDAR hypofunction theory, evidence has been accumulating to show that abnormalities in NO level are in fact associated with schizophrenia Trevlopoulou et al., "The nitric oxide donor sodium nitroprusside attenuates recognition memory deficits and social withdrawal produced by the NMDA receptor antagonist ketamine and induces anxiolytic-like behaviour in rats" *Psychopharmacology (Berl)* 233(6): 1045-1054 (2016) Whether pathology of schizophrenia lies on the over- or underproduction of NO is still under debate, but the implications of NO in schizophrenia are well studied and documented from various perspectives.

Schizophreniform disorder is a mental disorder diagnosed when symptoms of schizophrenia are present for a significant portion of the time within a one-month period, but signs of disruption are not present for the full six months required for the diagnosis of schizophrenia. The symptoms of both disorders can include delusions, hallucinations, disorganized speech, disorganized or catatonic behavior, and social withdrawal. While impairment in social, occupational, or academic functioning is required for the diagnosis of schizophrenia, in schizophreniform disorder an individual's level of functioning may or may not be affected. While the onset of schizophrenia is often gradual over a number of months or years, the onset of schizophreniform disorder can be relatively rapid.

B. Depression and Depressive Disorders

Major depressive disorder (MDD), also known simply as depression, is a mental disorder characterized by at least two weeks of low mood that is present across most situations. It is often accompanied by low self-esteem, loss of interest in normally enjoyable activities, low energy, and pain without a clear cause. People may also occasionally have false beliefs or see or hear things that others cannot. Some people have periods of depression separated by years in which they are normal while others nearly always have symptoms present. Major depressive disorder can negatively affect a person's personal, work, or school life, as well as sleeping, eating habits, and general health. Between 2-7% of adults with major depression die by suicide, and up to 60% of people who die by suicide had depression or another mood disorder. Richards et al., (2014) In: The Oxford Handbook of Depression and Comorbidity. Oxford University Press. p. 254. ISBN 9780199797042; American Psychiatric Association (2013), In: Diagnostic and Statistical Manual of Mental Disorders (5th ed.), Arlington: American Psychiatric Publishing, pp. 160-168; and Lynch et al., (2010) In: Forensic Nursing Science. Elsevier Health Sciences. p. 453.

Typically, people with depression are treated with counseling and antidepressant medication. Medication appears to be effective, but the effect may only be significant in the most severely depressed. Fournier et al., "Antidepressant drug effects and depression severity: a patient-level meta-analysis" *JAMA*. 303(1):47-53. (2010); Kirsch et al., "Initial severity and antidepressant benefits: a meta-analysis of data submitted to the Food and Drug Administration". *PLoS Med.* 5(2): e45 (2008). Counseling including cognitive behavioral therapy (CBT) and interpersonal therapy are also employed. Driessen et al., "Cognitive Behavioral Therapy for Mood Disorders: Efficacy, Moderators and Mediators". *Psychiatric Clinics of North America*. 33(3):537-555 (2010).

Conflicting results have arisen from studies that look at the effectiveness of antidepressants in people with acute, mild to moderate depression. Stronger evidence supports the usefulness of antidepressants in the treatment of depression that is chronic (dysthymia) or severe. While small benefits were found, it is believed that they may be due to issues with the trials rather than a true effect of the medication. Kirsch et al., "The emperor's new drugs: An analysis of antidepressant medication data submitted to the U.S. Food and Drug Administration". *Prevention & Treatment* Vol. 5 (2002). It has also been suggested that the overall effect of new-generation antidepressant medications are below recommended criteria for clinical significance. Fournier et al., "Antidepressant drug effects and depression severity: a patient-level meta-analysis" *JAMA*. 303(1):47-53 (2010); Kirsch et al., "Initial severity and antidepressant benefits: a meta-analysis of data submitted to the Food and Drug Administration". PLoS Med. 5(2): e45 (2008).

C. Bipolar and Related Disorders

Bipolar disorder is characterized by periods of depression and periods of elevated mood. The elevated mood is significant and is known as mania or hypomania, depending on its severity, or whether symptoms of psychosis are present. During mania, an individual behaves or feels abnormally energetic, happy, or irritable. Individuals often make poorly thought out decisions with little regard to the consequences. The need for sleep is usually reduced during manic phases. During periods of depression, there may be crying, a negative outlook on life, and poor eye contact with others. The risk of suicide among those with the illness is high at greater than 6 percent over 20 years, while self-harm occurs in 30-40 percent. Other mental health issues such as anxiety disorders and substance use disorder are commonly associated. Anderson et al., "Bipolar disorder". *Br. Med J* 345: e8508 (2012); and American Psychiatry Association, *Diagnostic and Statistical Manual of Mental Disorders* (5th ed.). Arlington: American Psychiatric Publishing. pp. 123-154 (2013).

Bipolar disorder treatment commonly includes psychotherapy, as well as medications such as mood stabilizers and antineuropsychiatrics. Examples of mood stabilizers that are commonly used include lithium and various anticonvulsants. Treatment in a hospital without the individual's consent may be required if a person is at risk to themselves or others but refuses treatment. Severe behavioral problems, such as agitation or combativeness, may be managed with short term antineuropsychiatrics or benzodiazepines. In periods of mania it is recommended that antidepressants be stopped. If treatments are stopped, it is recommended that this be done slowly. The risk of death from natural causes such as heart disease is twice that of the general population. This is believed due to poor lifestyle choices and the side effects from medications.

D. Delusional Disorders

Delusional disorder is a mental illness in which the patient has no accompanying prominent hallucinations, thought disorder, mood disorder, or significant flattening of affect. Delusions are a specific symptom of psychosis. Delusions can be "bizarre" or "non-bizarre" in content; non-bizarre delusions are fixed false beliefs that involve situations that could potentially occur in real life, such as being followed or poisoned. Apart from their delusions, people with delusional disorder may continue to socialize and function in a normal manner and their behavior does not necessarily generally seem odd. However, the preoccupation with delusional ideas can be disruptive to their overall lives. Semple D. "Oxford Hand Book of Psychiatry" Oxford Press. (2005) p 230; American Psychiatric Association. (2013). Diagnostic and Statistical Manual of Mental Disorders, (5th ed., text revision), Washington, D.C.; American Psychiatric Association; Hales E and Yudofsky J A, eds, The American Psychiatric Press Textbook of Psychiatry, Washington, D.C.: American Psychiatric Publishing, Inc., (2003); and Winokur, George. "Comprehensive Psychiatry-Delusional Disorder" American Psychiatric Association. 1977. p 513.

For a diagnosis to be made, auditory and visual hallucinations cannot be prominent, though olfactory or tactile hallucinations related to the content of the delusion may be present. The Diagnostic and Statistical Manual of Mental Disorders (DSM) defines six subtypes of the disorder characterized as: i) erotomanic (believes that someone is in love with them); ii) grandiose (believes that they are the greatest, strongest, fastest, richest, or most intelligent person ever); iii) jealous (believes that the love partner is cheating on them): iv) persecutory (delusions that the person or someone to whom the person is close is being malevolently treated in some way); v) somatic (believes that they have a disease or medical condition); and vi) mixed—having features of more than one subtype.

A challenge in the treatment of delusional disorders is that most patients have limited insight, and do not acknowledge that there is a problem. Most patients are treated as outpatients, although hospitalization may be required in some cases if there is a risk of harm to self or others. Individual psychotherapy is recommended rather than group psychotherapy, as patients are often quite suspicious and sensitive. Antineuropsychiatrics are not well tested in delusional disorder, but they do not seem to work very well, and often have no effect on the core delusional belief. Antineuropsychiatrics may be more useful in managing agitation that can accompany delusional disorder. Until further evidence is found, it seems reasonable to offer treatments which have efficacy in other neuropsychiatric disorders. Skelton et al., "Treatments for delusional disorder" *Cochrane Database Syst Rev.* 22(5) CD009785 (2015).

E. Schizotypal Personality Disorder

Schizotypal personality disorder (STPD) or schizotypal disorder is a mental disorder characterized by severe social anxiety, thought disorder, paranoia, hallucination, derealization, transient psychosis and often unconventional beliefs. People with this disorder feel extreme discomfort with maintaining close relationships with people, mainly because they think that their peers harbor negative thoughts towards them, so they avoid forming them. Peculiar speech mannerisms and odd modes of dress are also symptoms of this disorder. Those with STPD may react oddly in conversations, not respond or talk to themselves. They frequently interpret situations as being strange or having unusual meaning for them; paranormal and superstitious beliefs are common. Such people frequently seek medical attention for anxiety or depression instead of their personality disorder. Schizotypal Personality Disorder (pp. 655-659). Diagnostic and Statistical Manual of Mental Disorders, Fifth Edition (2013).

Treatment is usually with the same drugs used to treat schizophrenia including traditional neuroleptics such as haloperidol and thiothixene. It has been suggested to distinguish between two basic groups of schizotypal patients: i) Schizotypal patients who appear to be almost schizophrenic in their beliefs and behaviors (aberrant perceptions and cognitions) are usually treated with low doses of antipsychotic medications, e.g. thiothixene; and ii) Schizotypal patients who are more obsessive-compulsive in their beliefs and behaviors, SSRIs like Sertraline appear to be more effective. Livesley. John W. (2001). Handbook of Personality Disorders: Theory. Research, and Treatment. The Guilford Press.

F. Schizoaffective Disorder

Schizoaffective disorder (SZA, SZD or SAD) is a mental disorder characterized by abnormal thought processes and deregulated emotions. [1][2] The diagnosis is made when the person has features of both schizophrenia and a mood disorder-either bipolar disorder or depression—but does not strictly meet diagnostic criteria for either alone.[1][2] The bipolar type is distinguished by symptoms of mania, hypomania, or mixed episode; the depressive type by symptoms of depression only. Malaspina et al., "Schizoaffective disorder in the DSM-5". *Schizophrenia Research* 150 (1): 21-25 (2013).

Common symptoms of the disorder include hallucinations, paranoid delusions, and disorganized speech and thinking. The onset of symptoms usually begins in young adulthood, currently with an uncertain lifetime prevalence because the disorder was redefined, but DSM-IV prevalence estimates were less than 1 percent of the population, in the range of 0.5 to 0.8 percent. Diagnosis is based on observed behavior and the person's reported experiences.

The mainstay of current treatment is antipsychotic medication combined with mood stabilizer medication or antidepressant medication, or both. There is growing concern by some researchers that antidepressants may increase psychosis, mania, and long-term mood episode cycling in the disorder. When there is risk to self or others, usually early in treatment, hospitalization may be necessary. Psychiatric rehabilitation, psychotherapy, and vocational rehabilitation are very important for recovery of higher psychosocial function.

G. Catatonia

Catatonia is a state of psychogenic motor immobility and behavioral abnormality manifested by stupor. Catatonia may be associated with other psychiatric conditions such as schizophrenia, bipolar disorder, post-traumatic stress disorder, depression and other mental disorders, narcolepsy, as well as drug abuse or overdose (or both). It may also be seen in many medical disorders including infections (such as encephalitis), autoimmune disorders, focal neurologic lesions (including strokes), metabolic disturbances, alcohol withdrawal and abrupt or overly rapid benzodiazepine withdrawal. People with catatonia may experience an extreme loss of motor skill or even constant hyperactive motor activity. Catatonic patients will sometimes hold rigid poses for hours and will ignore any external stimuli. People with catatonic excitement can suffer from exhaustion if not treated. Patients may also show stereotyped, repetitive movements. They may show specific types of movement such as waxy flexibility, in which they maintain positions after being placed in them by someone else. Conversely, they may remain in a fixed position by resisting movement in proportion to the force applied by the examiner. They may repeat meaningless phrases or speak only to repeat what is heard.

IV. Therapeutics

A. NMDAR Potentiation

Given the widely accepted NMDAR hypo-function hypothesis in schizophrenia pathogenesis, a number of compounds have been investigated to potentiate NMDAR activity, thereby enhancing its downstream effects. These compounds include: full agonists of the glycine co-agonist site of NMDA (e.g. glycine, D-Alanine, and D-Serine), partial agonist of the glycine site (e.g. D-clycloserine), inhibitor of glycine reuptake via glycine transporter-1 (e.g. sarcosine), and acylated prodrug of glycine (e.g. milocemide). The efficacy of these compounds appears to be modest at most; each drug has its distinct therapeutic limitations. Further, their interaction with currently available antipsychotic medications remain unclear (52). Table 3 summarizes the Six compounds that have been studied.

TABLE 3

Compounds studied for schizophrenia treatment through N-methyl-D-aspartate receptor (NMDAR) potentiation

| Compound | Mechanism | Finding | Limitation |
| --- | --- | --- | --- |
| Glycine (72-79) | Full agonist of NMDA-glycine site | Improvement in overall psychopathology and positive symptoms | Impermeable to blood brain barrier (BBB)/low central nervous system (CNS) bioavailability High doses required to reach therapeutic effects |

TABLE 3-continued

Compounds studied for schizophrenia treatment through N-methyl-D-aspartate receptor (NMDAR) potentiation

| Compound | Mechanism | Finding | Limitation |
|---|---|---|---|
| D-Alanine (80) | Full agonist of NMDA-glycine site | Improvement in overall psychopathology and positive symptoms and negative symptoms | Limited data<br>Lower permeability than D-serine, so higher doses needed |
| D-Serine (81-85) | Full agonist of the NMDA-glycine site Reversed agent of NMDAR antagonist | Improvement in overall psychopathology, negative symptoms and cognition | Nephrotoxicity<br>D-serine is a dominant co-antagonist for NMDAR-elicited neurotoxicity in hippocamped organotype slices |
| D-Cycloserine (86-98) | Partial agonist at NMDA-glycine site | Inconsistent finding; improvement in negative symptoms | Very narrow therapeutic window<br>Worsening of symptoms in combination with clozapine<br>Decrease in efficacy over time |
| Sarcosine (99-101) | Inhibition of glycine transporter-1 (GlyT-1) | Improvment in overall psychopathology and negative symptoms | No improvement in positive symptoms in combination with independance<br>Possible drug-drug interaction with antipsychotics |
| Milacemide (102, 103) | Acylated prodrug of glycine | No significant clinical benefit | Limited data<br>Optimal dosing nuclear |

B. NO Supplementation

As NO is able to cross the blood brain barrier (BBB), it was proposed that peripheral intravenous infusion of sodium nitroprusside (SNP), a prodrug that releases NO when metabolized, would be able to bypass the hypo-functioning NMDAR and directly increase the intracellular levels of NO. A prompt improvement of acute schizophrenia symptoms after a single four-hour intravenous infusion of SNP (0.5 μkg/min) has been reported. In this randomized, double-blinded, placebo-controlled trial of 20 patients with schizophrenia, significant improvement of positive, negative, anxiety, and depressive symptoms was shown to be both rapid (within two hours of infusion) and persistent (at least four weeks after infusion). Hallak et al. "Rapid improvement of acute schizophrenia symptoms after intravenous sodium nitroprusside: a randomized, double-blind, placebo-controlled trial" *JAMA Psychiatry* (2013) 70(7):668-676; and Coyle J T., "Nitric oxide and symptom reduction in schizophrenia" *JAMA Psychiatry* (2013) 70(7):664-665.

A replication study in 20 patients with schizophrenia, however, revealed that intravenous infusion of SNP did not lead to any reduction in schizophrenia symptoms or cognitive performance—both immediately after the infusion and four weeks later. The discrepant findings were attributed to a longer history of schizophrenia and less severe negative symptoms of the study sample, as compared to previously reported trials. The possibility of varying therapeutic effects conferred by NO supplementation based on the disease phase and symptom domains has therefore been postulated. Stone et al., "The effect of sodium nitroprusside on psychotic symptoms and spatial working memory in patients with schizophrenia: a randomized, double-blind, placebo-controlled trial" *Psychol Med*. (2016) 46(16):3443-3450.

While the idea of NO donor-based treatment is intriguing, the conflicting results in the two published SNP trials suggest that more sophisticated considerations beyond simple NO supplementation might be missing. One of such considerations could be related to NOS uncoupling.

V. Pharmaceutical Compositions and/or Formulations

The present invention further provides pharmaceutical compositions and/or formulations (e.g., comprising the compounds described above). The pharmaceutical compositions of the present invention may be administered in a number of ways depending upon whether local or systemic treatment is desired and upon the area to be treated. Administration may be topical (including ophthalmic and to mucous membranes including vaginal and rectal delivery), pulmonary (e.g., by inhalation or insufflation of powders or aerosols, including by nebulizer; intratracheal, intranasal, epidermal and transdermal), oral or parenteral. Parenteral administration includes intravenous, intraarterial, subcutaneous, intraperitoneal or intramuscular injection or infusion; or intracranial, e.g., intrathecal or intraventricular, administration.

Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable.

Compositions and formulations for oral administration include powders or granules, suspensions or solutions in water or non-aqueous media, capsules, sachets or tablets. Thickeners, flavoring agents, diluents, emulsifiers, dispersing aids or binders may be desirable.

Compositions and formulations for parenteral, intrathecal or intraventricular administration may include sterile aqueous solutions that may also contain buffers, diluents and other suitable additives such as, but not limited to, penetration enhancers, carrier compounds and other pharmaceutically acceptable carriers or excipients.

Pharmaceutical compositions of the present invention include, but are not limited to, solutions, emulsions, and liposome-containing formulations. These compositions may be generated from a variety of components that include, but are not limited to, preformed liquids, self-emulsifying solids and self-emulsifying semisolids.

The pharmaceutical formulations of the present invention, which may conveniently be presented in unit dosage form, may be prepared according to conventional techniques well known in the pharmaceutical industry. Such techniques include the step of bringing into association the active ingredients with the pharmaceutical carrier(s) or excipient(s). In general the formulations are prepared by uniformly and intimately bringing into association the active ingredients with liquid carriers or finely divided solid carriers or both, and then, if necessary, shaping the product.

The compositions of the present invention may be formulated into any of many possible dosage forms such as, but not limited to, tablets, capsules, liquid syrups, soft gels, suppositories, and enemas. The compositions of the present invention may also be formulated as suspensions in aqueous, non-aqueous or mixed media. Aqueous suspensions may further contain substances that increase the viscosity of the suspension including, for example, sodium carboxymethylcellulose, sorbitol and/or dextran. The suspension may also contain stabilizers.

In one embodiment of the present invention the pharmaceutical compositions may be formulated and used as foams. Pharmaceutical foams include formulations such as, but not limited to, emulsions, microemulsions, creams, jellies and liposomes. While basically similar in nature these formulations vary in the components and the consistency of the final product. Agents that enhance uptake of oligonucleotides at the cellular level may also be added to the pharmaceutical and other compositions of the present invention. For example, cationic lipids, such as lipofectin (U.S. Pat. No. 5,705,188), cationic glycerol derivatives, and polycationic molecules, such as polylysine (WO 97/30731), also enhance the cellular uptake of oligonucleotides.

The compositions of the present invention may additionally contain other adjunct components conventionally found in pharmaceutical compositions. Thus, for example, the compositions may contain additional, compatible, pharmaceutically-active materials such as, for example, antipruritics, astringents, local anesthetics or anti-inflammatory agents, or may contain additional materials useful in physically formulating various dosage forms of the compositions of the present invention, such as dyes, flavoring agents, preservatives, antioxidants, opacifiers, thickening agents and stabilizers. However, such materials, when added, should not unduly interfere with the biological activities of the components of the compositions of the present invention. The formulations can be sterilized and, if desired, mixed with auxiliary agents, e.g., lubricants, preservatives, stabilizers, wetting agents, emulsifiers, salts for influencing osmotic pressure, buffers, colorings, flavorings and/or aromatic substances and the like which do not deleteriously interact with the nucleic acid(s) of the formulation.

Dosing is dependent on severity and responsiveness of the disease state to be treated, with the course of treatment lasting from several days to several months, or until a cure is effected or a diminution of the disease state is achieved. Optimal dosing schedules can be calculated from measurements of drug accumulation in the body of the patient. The administering physician can easily determine optimum dosages, dosing methodologies and repetition rates. Optimum dosages may vary depending on the relative potency of individual oligonucleotides, and can generally be estimated based on EC50s found to be effective in in vitro and in vivo animal models or based on the examples described herein. In general, dosage is from 0.01 µg to 100 g per kg of body weight, and may be given once or more daily, weekly, monthly or yearly. The treating physician can estimate repetition rates for dosing based on measured residence times and concentrations of the drug in bodily fluids or tissues. Following successful treatment, it may be desirable to have the subject undergo maintenance therapy to prevent the recurrence of the disease state, wherein the compound is administered in maintenance doses, ranging from 0.01 µg to 100 g per kg of body weight, once or more daily, to once every 20 years.

EXPERIMENTAL

Example 1

Minocycline Clinical Trial for a Neuropsychiatric Disorder Treatment

This example presents data showing that therapeutic effect of minocycline, believed to reduce NOS expression, is not mediated via modulation of nitric oxide production.
Participants
Adult patients with schizophrenia were recruited from the 1st Affiliated Hospital of Kunming Medical University, and the Mental Health Center of Yunnan Province, China, between June 2010 and November 2011. The diagnosis of schizophrenia was made by trained clinical interviewers using the structured clinical interview for DSM-IV diagnosis (SCID). First et al., In: Structured Clinical interview for DSM-IV Axis I Disorders-Clinician Version (SCID-CV). Washington, D.C.: American Psychiatry Press. (1996). Other inclusion criteria included: (1) age 18 to 40 years old; (2) disease duration ≤5 years; (3) on stable dose of risperidone for at least 4 weeks prior to screening; (4) a stable living arrangement. Exclusion criteria were: (1) being allergic to minocycline or tetracycline; (2) a psychiatric diagnosis other than schizophrenia (determined by SCID); (3) serious, unstable medical conditions; (4) diagnosis of diabetes mellitus; (4) female patients who were planning to become pregnant, or were pregnant or lactating were also excluded from the study. The study was approved by the ethics committee of the 1st Affiliated Hospital of Kunming Medical University.
Procedures
After screening, each eligible subject underwent baseline assessments including the Scale for the Assessment of Negative Symptoms (SANS), the Positive and Negative Syndrome Scale (PANSS), and blood draw for lab tests. Andreasen N C., "Negative symptoms in schizophrenia: Definition and reliability" *Arch. Gen. Psychiatry* 39:784-788 (1982); and Kay et al., "The positive and negative syndrome scale (PANSS) for schizophrenia" *Schizophr. Bull.* 13:261-276 (1987). Subjects continued to take risperidone at the same dose throughout the study, and were randomized in a 1:1 ratio to receive either minocycline (200 mg per day) or placebo for 16 weeks. At week 16, baseline assessments were repeated.
Measures
Anthropometric measures included weight, height and body mass index (BMI). Blood samples were obtained 11 h (±1 h) after the completion of the last meal the night before. Subjects were allowed to drink water during the fasting period. Laboratory assays for plasma levels of TNFα, and IL-1β were performed using the enzyme-linked immunosorbent assay (ELISA) (Bender Med Systems GmbH Campus Vienna Biocenter 2 A-1030 Vienna, Austria, Europe). Plasma levels of NO metabolites (nitrites and nitrates) were measured using the Griess method (Cortas & Wakid 1990) (Nanjing Jiancheng Bioengineering Institute, China).
Statistical Analysis
Statistical analysis was performed using SPSS (version 24.0, IBM Corp, Armonk, N.Y.). Descriptive statistics were performed to summarize demographic and clinical characteristics of the study sample. Group comparisons were performed using the independent t test for continuous variables, and the Fisher exact test or Chi-square test for categorical variables. Analysis of covariance (ANCOVA) was used to compare change scores from baseline to week 16 between the two treatment groups controlling for baseline scores and potential confounding variables. For all analyses, a p value less than 0.05 (2-tailed) was used for statistical significance.

Example 2

L-Arginine/Tetrahydrobiopterin Clinical Trial for a Neuropsychiatric Disorder Treatment This example presents data that will show that therapeutic effect of the combined administration of L-arginine and tetrahydrobiopterin (BH4) to patients with a neuropsychiatric disorder (e.g., schizophrenia) by recoupling an uncoupled NOS pathway. In other words, the combination therapy re-establishes the homeostatic activity of an NOS pathway such that the production of nitric oxide is properly regulated.

Cross Over Design

The overall study design will enroll approximately fifteen (15) patients with moderately severe schizophrenia symptoms and compare two treatment conditions: 1) L-arginine plus BH4; and 2) a respective placebo. The combination will be administered as a liquid or powder comprising 6 g/day L-arginine and 500 mg/day BH4. The following treatment regimen will be followed:

i) three-week treatment (condition 1),
ii) 4-week washout,
iii) 3-week treatment (condition 2)

Treatment Efficacy Assessment

Psychiatric symptoms will be measured at baseline, week 6 and week 12 using the Positive and Negative Symptoms Scale (PANSS), the Schedule for the Assessment of Negative Symptoms (SANS), the Calgary Depression Rating Scale (CDRS), and the Clinical Global Impression Scale (CGI), and the Columbia Suicide Severity Rating Scale (CSSRS); 2) quality of life as measured by the Heinrichs Carpenter Quality of Life Scale (QOL).

Nitric Oxide Bioavailability and Function Assessment

NO concentration in blood, breath and urine will be measured using a Sievers Nitric Oxide Analyzer (NOA280i). Brachial artery flow-mediated vasodilation (FMD) will be determined using EndoPAT which uses finger plethysmography to evaluate changes in pressure in the non-dominant arm before and after 5 minutes of brachial artery occlusion on the upper arm.

Blood Biomarkers

Inflammatory biomarkers including GSH, hsCRP, IL-6 an TNFα will be measured.

Safety and Side Effects Assessment

A thorough medical history, physical exam, pregnancy test for female, urine drug screen will be done during the screening visit. ECG, the comprehensive metabolic panel will be done at screening and week 3. Vital signs will be measured at screening and every weekly visit. Side effects will be monitored at baseline and weekly using the Systematic Assessment for Treatment Emergent Events (SAFTEE). The SAFTEE begins with the open-ended general inquiry, and then presents questions in 23 categories of possible side effects organized according to organ system or body region, with a total of 78 specific questions.

Extrapyramidal symptoms (EPS) will be evaluated at baseline and week 3 using the Simpson-Angus Scale, the Barnes Akathisia Scale and the Abnormal Involuntary Movement Scale (AIMS).

Example 3

Adjunctive L-Arginine/Tetrahydrobiopterin in Patients with Treatment Resistant Schizophrenia This example presents a study protocol that will be performed to assess the efficacy of an L-arginine/tetrahydrobiopterin combination for treatment resistant schizophrenia.

1. Study Timeline

Screening Visit

After signing a HIPAA compliant informed consent form, subjects will undergo a review of medical history and concomitant medications, and a physical exam. The MINI International Neuropsychiatric Interview will be performed to confirm the psychiatric diagnosis. Subjects will also have a urine drug screen, urine pregnancy test, CBC, CMP, vital signs, 12-lead ECG.

Baseline Visit

Within 2 weeks after the screening visit, eligible subjects will undergo: 1) vital signs; 2) efficacy assessment battery; 3) safety assessment battery; 4) NO levels in blood, breath and urine using Sievers NO Analyzer (NOA280i); 5) brachial artery flow-mediated vasodilation (FMD, an indicator of NO function) using EndoPAT; 6) blood biomarkers for inflammation and oxidative stress, including glutathione (GSH), glutathione disulfide (GSSG), high sensitivity C reactive protein (hsCRP), interleukin 6 (IL-6) and tumor necrosis factor α (TNFα). On a separate day, subjects will go to the UMass Research MRI Center to complete the MRS procedure. Then they will receive one week supply of study medication.

Week 1 Visit

Vital signs will be assessed. Treatment compliance and possible adverse effects will be evaluated. Subjects will receive one week supply of study medication.

Week 2 Visit

Subjects will undergo: 1) vital signs; 2) efficacy assessment battery; 3) safety assessment battery; 4) NO levels in blood, breath and urine; 5) brachial artery FMD; 6) blood biomarkers for inflammation and oxidative stress, including GSH, GSSG, hsCRP, IL-6 and TNFα. On a separate day, subjects will go to the UMass Research MRI Center to complete the MRS procedure.

Early Termination Visit

Subjects will undergo: 1) vital signs; 2) safety assessment battery; 3) CBC and CMP.

2. Study Population a. Subject Eligibility

Inclusion Criteria

Each subject must meet all of the following criteria to be eligible for this study:

Males or Females aged 18-65 years inclusive.
Primary diagnosis of Schizophrenia established by a structured psychiatric evaluation (MINI) based on Diagnostic and Statistical Manual of Mental Disorders Fifth Edition (DSM-V) criteria.
Written informed consent in compliance with 21 CFR part 50 and in accordance with the International Conference on Harmonization (ICH) Good Clinical Practice (GCP) Guidelines.
A Positive and Negative Syndrome Scale (PANSS) (Kay et al 1987) total score≥70 with a score of ≥4 on two or more of the following PANSS items: delusions, conceptual disorganization, hallucinatory behavior, suspiciousness, and unusual thought content.

A score of ≥4 on the Clinical Global Impression-Severity (CGI-S) (Guy, 1976).

Must have ongoing antipsychotic treatment for at least 8 weeks, with a stable dose for at least 4 weeks. Subjects who have failed to achieve clinically-recognized symptom reduction to at least 1 marketed antipsychotic agent, given at a Physician Desk Reference (PDR)-defined therapeutic dose for ≥8 weeks during the past 12 months, will be eligible.

Women of childbearing potential must have a negative pregnancy test performed at screening visit prior to randomization. Women enrolled in this trial must use adequate birth control.

Understands and is able, willing, and (in the opinion of the investigator) likely to fully comply with the study procedures and restrictions.

Exclusion Criteria

Subjects who meet any of the following criteria will be excluded from the study.

Subjects with a history of renal insufficiency, congestive heart failure, cardiac arrhythmias or history of myocardial infarction, liver cirrhosis, guanidinoacetate methyltransferase deficiency, herpes.

Subjects with any clinically significant abnormalities as determined by medical history, physical exam, clinical and lab evaluation suggestive of an underlying disease state that may, in the opinion of the investigator, confound the results of study, increase risk to the subject, or lead to difficulty complying with the protocol.

Subjects with the lab values defined as exclusionary safety values in Table 4.

On medications known to inhibit folate metabolism (e.g., methotrexate).

On medications known to affect NO-mediated vaso-relaxation (e.g., PDE-5 inhibitors such as sildenafil, vardenafil, or tadalafil).

Subjects on nitrates.

Subjects on levodopa.

Subjects on antihypertensive medications (such as ACE inhibitors, angiotensin receptor blockers, isoproterenol, potassium-sparing diuretics).

Subjects on antidiabetes medications.

Subjects on anticoagulant/antiplatelet medications.

Subjects with a current (within the last 3 months) DSM-V diagnosis of alcohol or substance use disorder (excluding nicotine and caffeine) as established by the clinical assessment (MINI) at the screening visit will be excluded.

Tested positive for the urine drug screen.

Subjects at imminent risk of suicide or injury to self or others, as per the opinion of the investigator, or history of significant suicide attempt within the last 6 months as per the Columbia Suicide Severity Rating Scale (C-SSRS).

Subjects that have taken an investigational drug or taken part in a clinical trial within 30 days prior to screening.

Known history of phenylketonuria (PKU).

Known hypersensitivity reactions (such as anaphylaxis and rash) to L-arginine and/or BH4.

Any other reason that, in the opinion of the investigator, would compromise patient safety or integrity of the study.

TABLE 4

Exclusionary Safety Values of Potential Clinical Concern

| Complete Blood Count | |
| --- | --- |
| Leukocytes | <2 or >17.5 × $10^3$/mm$^3$ |
| Platelets | <75 or >700 × $10^3$/mm$^3$ |
| Comprehensive Metabolic Panel | |
| Sodium | <1.1 times the lower limit or >1.1 times upper limit of the reference range |
| Potassium | <1.1 times the lower limit or >1.1 times upper limit of the reference range |
| Blood Urea Nitrogen (BUN) | >1.3 times upper limit of the reference range |
| Creatinine | >1.3 times upper limit of the reference range |
| Glomerular Filtration Rate | <60 |
| Aspartate amino transferase (AST) | >3 times upper limit of the reference range |
| Alanine amino transferase (ALT) | >3 times upper limit of the reference range |

3. Subject Recruitment

Potential subjects will be recruited from Community Healthlink (CHL, located at 72 Jacques Avenue) and the Ambulatory Psychiatry Clinic (located at 26 Queen Street & UMass Hahnemann Campus). Members of the study team will be stationed at these sites to help facilitate recruitment. All research staff will have access to electronic medical records of patients at these outpatient departments. CHL is the largest, multi-service, private, non-profit mental health organization in central Massachusetts with 5,000 outpatients over 18 years of age. CHL cares for many with severe and persistent mental illness. Approximately 1,000 individuals are diagnosed with schizophrenia or schizoaffective disorder, and 700 with bipolar disorder. Dr. Fan is the Director of the Schizophrenia Specialty Clinic and the Screening and Treatment of Early Psychosis (STEP) Clinic at CHL. Currently CHL has about 200 active schizophrenia patients. The Ambulatory Psychiatric Clinic serves patients aged 18 and up. The clinic handles more than 40,000 visits per year. Patients come from a wide range of socioeconomic backgrounds. Due to the patient population at this site, the research team will have access to many eligible patients.

The study will be advertised via IRB-approved fliers and brochures which will be placed at strategic locations at CHL and across the UMass Medical School campus. The study will also be advertised via fliers and brochures at local homeless shelters, various group homes, bus stops, and grocery stores in the Central Massachusetts area. We will also advertise at various private practice clinics, local hospitals, peer support centers, and club houses in the Worcester area. We will also distribute IRB-approved fliers and brochures to selected locations in the broader Central Massachusetts area, including towns surrounding the Greater Boston area.

Consenting Process

Subjects will sign a HIPAA-compliant informed consent form (ICF) before any study related screening procedures are performed. An overview of the study objectives and a summary of study procedure will be explained to the subject prior to signing the ICF. At any point during the study, subject will be encouraged to seek answers to any questions they may have. We have developed a questionnaire consisting of approximately 10 true-false questions about important aspects of the study procedures, potential risks, the subject's right to end participation at any time or to speak to a patient advocate, etc. Subjects must score a 100% to participate in the study. Subjects who are judged to be competent will then be asked to sign the study consent form. In addition, prior to starting the study medication, the PI or co-Investigator will meet with each subject to review the risks of taking the study medication, as well as which medications should be avoided while taking the LB combination study medication.

A diverse patient population is expected. If the subject lacks the capacity to provide informed consent, then the subject's authorized legal guardian will be present for the consent process. Potential participants and guardians are encouraged to read the consent form and ask questions. After providing a detailed overview of the study, the study coordinator will present the questionnaire consisting of 10 true-false questions about important aspects of the study procedures, potential risks, the subject's right to end participation at any time or to speak to a patient advocate, etc. to the subject and the subject's authorized legal guardian. Participants are further encouraged to solicit input from significant others and/or care providers, if appropriate. To minimize coercion, the consent form has language that clearly spells out that participation in the study is voluntary and refusal to participate will not affect a person's health/mental health care. The subject's authorized legal guardian will be required to sign the informed consent form, and both the patient and their authorized legal guardian will be required to complete the true-false questionnaire form if they agree to participate. We will explain the study in a language understandable to the subject and obtain his or her assent. Subject will be particularly closely monitored. Subject will be withdrawn if they appear unduly distressed.

4. Assessment Procedures

Medical History

A detailed medical history will be obtained by the PI or designee during the screening visit. This will include information regarding the subject' full history of medical and psychiatric conditions, diagnoses, procedures, treatments, demographic information, and any other noteworthy medical information, including suicidality, with dates of start and finish. Any updates to medical history information that the PI or designee becomes aware of will be captured throughout the study. Medical records will also be requested from the participant's primary care physician for confirmation of relevant eligibility criteria.

Physical Exam

The PI, or medically qualified designee, will perform the physical exam at the screening visit. If any clinically significant change is noted from screening, it will be reported as an AE and will be followed up to resolution or upon reaching a stable end point.

Vital Signs

Evaluation of vital signs will be performed by qualified personnel after the subject has been supine for 5 minutes, and will include a measurement of systolic and diastolic blood pressure, pulse rate, and oral temperature. Systolic and diastolic blood pressure should be then measured from supine to standing to assess orthostatic hypotension. Vital sign measurements will be obtained at the time points indicated in the schedule of events (SOE). Blood pressure should be taken on the same arm throughout the study.

If clinically significant findings, as determined by the PI or medically qualified designee, occur in any vital sign measurement, that measurement should be captured as an adverse event and will be repeated at medically appropriate intervals until the value returns to an acceptable range, a specific diagnosis is established, or the condition is otherwise explained.

5. Laboratory Assays

Fasting blood samples will be obtained and laboratory tests will be performed at the time points indicated in the SOE.

Complete Blood Count (CBC)

White blood cell (WBC) count with differential (absolute neutrophil count, lymphocytes, monocytes, basophils, and eosinophils), red blood cell (RBC) count, hemoglobin (Hgb), hematocrit (Hct), and platelet count.

Comprehensive Metabolic Panel (CMP)

Glucose, sodium, potassium, calcium, chloride, carbon dioxide, blood urea nitrogen (BUN), creatinine, calculated glomerular filtration rate, uric acid, phosphorus, magnesium, total protein, albumin, aspartate amino transferase (AST), alanine amino transferase (ALT), alkaline phosphatase (ALP), total bilirubin.

Blood Levels of GSH, GSSG, hsCRP, IL-6, TNFα

Blood samples for GSH, GSSG, hsCRP, IL6 and TNF-alpha will be collected and stored at −80 F. The tests will be run in batch at the UMass Memorial labs.

NO Levels in Blood, Breath and Urine

The Sievers Nitric Oxide Analyzer (NOA280i) offers the most versatile detection system for NO analysis. Using GE Analytical Instruments' highly sensitive, ozone-chemiluminescence technology, the NOA 280i has unsurpassed versatility for liquid and exhaled breath NO measurement. With over 700 publications using the Sievers Nitric Oxide Analyzer, the NOA 280i has proven to be the instrumentation of choice by researchers worldwide. The NOA 280i measures NO, nitrite, nitrate or nitrosothiols in most biological samples. Concentrations, ranging from low nanomolar to millimolar levels, can be measured in sample volumes ranging from a few microliters to several milliliters. In addition, exhaled NO can easily be measured with the NOA 280i. Fast response time and low sample flow rates allow for measurement of exhaled NO in humans and animals. The NO levels will be measured at Dr. Lou Messina's lab.

Glutamate and GABA Levels in the Brain

Neuroimaging data will be acquired using a 3.0 Tesla Philips Achieva whole-body MR system (Philips Healthcare, Best, The Netherlands) with an eight-element phased-array head coil at the U Mass Research MRI Center. T1-weighted anatomical MRI (MPRAGE sequence, 256× 256 voxels; TR: 6.985 msec; TE: 3.15 msec; field of view [FOV]: 240 mm×256 mm×180 mm; 180 slices) will be collected for diagnostic and localization purposes. 1H-MRS data will be acquired using the single voxel PRESS (TE: 28 msec; TR: 2000 msec; 128 averages) to quantify brain glutamate levels and MEGA-PRESS (TE: 68 msec; TR: 2000 msec; 16 averages×20 dynamic scans) to quantify brain GABA levels. Voxels (PRESS: 20 mm×20 mm×20 mm; MEGA-PRESS: 30 mm×30 mm×20 mm) will be placed in the bilateral pregenual ACC.

Brachial Artery Flow-Mediated Vasodilation (FMD)

The EndoPAT device will be used to measures FMD. The EndoPAT uses finger plethysmography to evaluate changes in pressure in the non-dominant arm before and after 5 minutes of brachia artery occlusion on the upper arm. Occlusion pressure will be set for at least 60 mmHg above systolic pressure. The hyperemic response will be measured for 5 minutes following release of the cuff. The FMD will be measured at Dr. Lou Messina's lab.

Urine Drug Screen

The test includes the following substances: opioids, cocaine, amphetamines, methadone, cannabinoids, barbiturates, benzodiazepines, methamphetamine, and phencyclidine.

Urine Pregnancy Test

The test will be performed in female subjects of childbearing potential using a dipstick urine test during the screening visit.

The PI, or medically qualified designee, should mark either "CS" for Clinically Significant or "NCS" for Not Clinically Significant in the margin of the laboratory result source document for items outside the normal range.

6. 12-Lead Electrocardiogram (EGG)

A 12-lead ECG will be taken at following a supine rest for 5 minutes. The ECGs will be reviewed by the P1 or medically qualified designee, and a cardiologist to assess any immediate abnormalities. The findings of the ECGs will be marked as normal, abnormal—not clinically significant, or abnormal-clinically significant.

The QTc will be calculated and recorded on a worksheet that will serve as the source document. All ECGs that are considered abnormal and clinically significant should be evaluated for a change from baseline and captured as an AE. If an ECG is considered abnormal and clinically significant, it will be reported as an AE.

7. Psychiatric Diagnostic Assessment

A Mini International Neuropsychiatric Interview (MINI v7.0) will be administered. The MINI 7.0 is a short clinician administered structured diagnostic interview for major psychiatric diagnoses in DSM-5 with an administration of around 20 minutes.

8. Efficacy Assessment Battery

The Positive and Negative Syndrome Scale (PANSS) (Kay et al 1987)

The PANSS will be used to measure symptom severity in this trial. The PANSS is a 30-item questionnaire used to evaluate schizophrenia symptoms, based on the clinical interview as well as reports of family members or primary care hospital workers. The PANSS consists of Positive Symptom subscale (7 items), Negative Symptom subscale (7 items), and General Psychopathology subscale (16 items). Each item is scored on a 7-point scale with higher scores representing increasing levels of psychopathology: 1) Absent, 2) Minimal, 3) Mild, 4) Moderate, 5) Moderate severe, 6) Severe, and 7) Extreme.

Scale for Assessment of Negative Symptoms (SANS) (Andreasen 1989)

The SANS assesses 5 domains: affective flattening, alogia, avolition/apathy, anhedonia/asociality, and attention. Within each domain, separate symptoms are related from 0 (absent) to 5 (severe).

Clinical Global Impressions-Severity (CGI-S) and Clinical Global Impressions-Improvement (CGI-I) Scales (Guy, 1976)

The CGI-S is an observer-rated scale that measures illness severity. The severity is measured using a 7 point Likert scale: 1) Normal, not at all ill, 2) Borderline mentally ill, 3) Mildly ill, 4) Moderately ill, 5) Markedly ill, 6) Severely ill, and 7) Among the most extremely ill patient. The CGI-I is an observer-rated scale that measures illness improvement. Improvement is measured using a 7 point Likert scale: 1) Very much improved, 2) Much improved, 3) Minimally improved, 4) No change 5) Minimally worse, 6) Much worse, 7) Very much worse.

9. Safety Assessment Battery

Adverse Events (AE)

Adverse events will be monitored at each study visit. The PI or medically qualified designee will review adverse events at every study visit. AE information is collected and recorded starting on the day the consent is signed until the end of an individual's participation in the study.

The Columbia Suicide Severity Rating Scale (C-SSRS) (Posner et al 2007)

The C-SSRS is a low-burden measure of the spectrum of suicidal ideation and behavior that was developed in the National Institute of Mental Health Treatment of Adolescent Suicide Attempters Study to assess severity and track suicidal events through any treatment. It is a clinical interview providing a summary of both ideation and behavior that can be administered during any evaluation or risk assessment to identify the level and type of suicidality present. The C-SSRS can also be used during treatment to monitor for clinical worsening. The C-SSRS will be performed to assess suicidal ideation and behavior. It contains a 1-to-5 rating scale for suicidal ideation of increasing severity (from a "wish list to die" to an "active thought of killing oneself with plan and intent"). The time frame is the past six months for the Baseline/Screening scale and since the last visit for the Since Last Visit scale.

10. Safety Profile of L-arginine and BH4

L-Arginine (Source of Information: Medlineplus.gov)

L-arginine will be provided by NOW Foods (Bloomingdale, Ill.). L-arginine is one of the most common natural amino acids. It is an α-amino acid that is naturally produced in humans. It is also available in many of the foods we eat including beef, pork, poultry, seafood and dairy products. L-arginine, which is readily available as an over-the-counter nutrition supplement, has been considered safe and well tolerated in general.

L-arginine should be used with caution in people with cirrhosis. People with guanidinoacetate methyltransferase deficiency, an inherited condition, are unable to convert arginine and other similar chemicals into creatine. To prevent complications associated with this condition, these people should not take arginine. There is a concern that L-arginine might make herpes worse. L-arginine might lower blood pressure.

BH4 (Source of Information: Kuvan Package Insert)

Kuvan is manufactured by BioMarin (San Rafael, Calif.). Sapropterin dihydrochloride, the active ingredient in Kuvan, is a synthetic preparation of the dihydrochloride salt of naturally occurring BH4. Kuvan was approved by the FDA in 2007 for the treatment of phenylketonuria (PKU). The safety of Kuvan was evaluated in 6 clinical studies in patients with PKU (aged 1 month to 50 years). In 4 studies, 579 patients received Kuvan in doses ranging from 5 to 20 mg/kg per day for lengths of treatment ranging from 1 to 164 weeks. The patient population was evenly distributed in gender, and approximately 95% of patients were Caucasian. Kuvan has an established safety profile. The most common adverse reactions (≥4% of patients) were headache, rhinorrhea, pharyngolaryngeal pain, diarrhea, vomiting, cough, and nasal congestion.

11. Evaluation of Adverse Events (AEs)

Definition

In accordance with International Conference on Harmonization (ICH) and Food and Drug Administration (FDA) guidance, any study related event incurred by a subject that occurs after the first study-related procedure to the completion of the protocol-defined safety surveillance period, that represents a change (positive or negative) in frequency or severity from a baseline (pre-study) event (if any), regardless of the presence of causal relationship or medical significance, is a reportable AE.

Abnormal results of diagnostic procedures, including laboratory test abnormalities, are considered AEs if they:

Result in discontinuation from the study,

Require treatment or any other therapeutic intervention,

Require further diagnostic evaluation (excluding a repetition of the same procedure to confirm the abnormality), or Are associated with clinical signs or symptoms that would have a significant clinical impact, as determined by the PI or medically qualified designee.

Performing an Adverse Events Assessment

The PI is ultimately responsible for assessing and reporting all adverse events as outlined in the protocol. The assessment of AEs may be delegated to a medically qualified designee, trained on this study protocol, who is listed on the FDA Form 1572 or equivalent document, and on the delegation of authority form. AEs should be volunteered by the subject, or solicited from the subjects using a standard statement, from examination of the subject at a clinic visit, or from observations of clinically significant lab values or special exam abnormal values. AEs will not be solicited by the use of a specific list of anticipated events.

All AEs are to be assessed and recorded in a timely manner and followed to resolution or until the Investigator determines that there is not an anticipated resolution. Each AE is to be documented with reference to severity, date of occurrence, duration, treatment, and outcome. Furthermore, each AE is to be classified as being serious or non-serious (as per definitions). In addition, the PI or delegated medically qualified Sub-Investigator must assess whether the AE is drug-related or not. Changes in severity of AEs and resolution dates should be documented as separate events.

Timing

AEs will be captured from the first study-related procedure through to the completion of the protocol defined safety surveillance period. For the purposes of this study, the period of observation for collection of AEs extends from the time the subject gives informed consent until the final visit.

Surgical procedures, planned before enrollment of the subject in the study, are not considered AEs if the condition was known before study inclusion. In this case the medical condition should be reported in the subject's medical history. Intermittent adverse events will not be reported as multiple adverse events. The definition of an intermittent adverse event is "a recurring event of consistent severity, frequency, and causality."

Severity

Each AE is to be documented with reference to severity. Changes in severity of AEs and resolution dates should be documented as separate events. Any event that ameliorates over more than one assessment time point may be considered for listing as a single event at the highest severity.

TABLE 5

Definition of Intensity of Adverse Events

| Intensity | Definition |
|---|---|
| Mild | Causes transient or mild discomfort; no limitation of usual activities; no medical intervention required. |
| Moderate | Causes mild to moderate limitation in activity; some limitation of usual activities: no or minimal medical intervention or therapy is required. |
| Severe | Causes marked limitation in activity; some assistance is usually required; medical intervention or therapy is required; hospitalization is probable. |

The term "severe" is often used to describe the intensity (severity) of a specific event (as in mild, moderate, or severe); the event itself, however, may be of relatively minor medical significance (such as a severe headache). This is not the same as "serious," which is based on subject/event outcome or action criteria usually associated with events that pose a threat to a subject's life or functioning. Seriousness (not severity) serves as a guide for defining regulatory reporting obligations.

Relationship

The PI or a medically qualified Sub-Investigator, trained on this study protocol, listed on the 1572 or equivalent document and on the delegation of authority form, is responsible for determining the adverse event relationship to the investigational product.

The following categories will be used to define the relationship of an AE to the administration of the IMP:

Not Related: Data are available to identify a clear alternative cause for the AE other than the investigational product.

Related: The cause of the AE is related to the investigational product and cannot be reasonably explained by other factors (e.g., the subject's clinical state, concomitant therapy, and/or other interventions).

Expectedness

An unexpected AE is any AE, the nature and severity of which is not consistent with the applicable product information (e.g., Package Insert of product characteristics for an approved product).

Clinical Significance

The PI or a medically qualified Sub-Investigator, trained on this study protocol who is listed on the 1572 or equivalent document and on the delegation of authority form, is responsible for determining the clinical significance of abnormal results (e.g., labs, ECG results) for the subject.

Clinical Laboratory Adverse Events

Changes in laboratory values or vital signs, or other safety parameters (e.g., ECG, study assessments) as noted in the protocol, are a subset of AEs and are reportable only if considered to be clinically significant by the PI or medically qualified Sub-Investigator.

Screening assessment exams are differentiated from adverse events/symptoms that are incurred post informed consent. Pre-dose abnormal results without clinical symptoms will not be reported as adverse events.

Pregnancy

If a subject (or subject's partner) becomes pregnant during the study, it must be reported in within 24 hours of the time the investigator becomes aware of the event and in accordance with the procedures described on the Pregnancy Report Form. Pregnancy in itself is not regarded as an AE unless there is a suspicion that a study drug may have interfered with the effectiveness of a contraceptive medication. Any pregnancy that occurs from Day 1 to 30 days following the last dose given will be followed for Serious Adverse Events (SAEs).

12. Evaluation of Serious Adverse Events (SAEs)

Definition

An SAE is defined by federal regulation as any AE occurring at any dose that results in any of the following outcomes:

Death
Life-threatening event
Hospitalization or prolongation of hospitalization
Persistent or significant disability/incapacity
Congenital anomaly/birth defect Reporting Serious Adverse Events The PI must inform the IRB immediately regarding any AE (does not have to be causally related) that is both serious and unexpected; or that represents a series of AEs that, on analysis, is unanticipated, or occurs at an unanticipated frequency, or otherwise represents an unanticipated safety risk to the study subject. The IRB may subsequently choose to modify the informed consent or request changes to the protocol.

Treatment-Emergent Adverse Events

A treatment emergent adverse event (TEAE) is an AE that either began following initiation of study treatment or was present prior to the initiation of the treatment, but increased in frequency or severity following initiation treatment, regardless of causality.

All TEAEs will be captured on the subject source documents for all required assessments on the CRF. The reporting PI or medically qualified Sub-Investigator will sign and date the CRF.

13. Protocol Waivers and Violations

Protocol Waivers

Protocol waivers will be assessed on a case by case basis by the PI for this study.

Procedure for Non-Compliant Subjects

Subjects who miss a study visit will be allowed (at the discretion of the PI) to make up that visit within a reasonable timeframe per the PI's judgement. Subjects who withdraw consent during the study will be asked to complete the early termination visit.

Protocol Deviation and Violation Definitions

Protocol violations as defined in the table below will be reported as described in the Manual of Operations.

TABLE 6

| | Major and Minor Protocol Violations | |
|---|---|---|
| | Major Protocol Violation | Minor Protocol Violation |
| Definition | A violation that may: Impact subject safety, Affect the integrity of study data, and/or Affect the subject's willingness to participate in the study. | A violation that doesnot: Impact subject safety, Compromise the integrity of study data, and/or Affect the subject's willingness to participate in the study. |
| Examples (not all-inclusive) | Failure to obtain informed consent Informed consent obtained by an unauthorized individual Enrollment of a subject who did not meet eligibility criteria for whom a protocol exception was not obtained Performing a study procedure that is not approved by the IRB and/or is not in the protocol Failure to perform a required lab test that, in the opinion of the Site Investigator, may affect subject safety or data integrity Failure to perform or follow a study procedure that, in the opinion of the Site Investigator, may affect subject safety or data integrity Failure to follow safety (AE) management plan Failure to report a SAE to the IRB and/or Coordination Center | Implementation of unapproved recruitment procedures Only a photocopy of the signed/dated consent form is available (the original is missing) Pages are missing from the signed/dated informed consent form Use of invalid consent form (i.e. without IRB approval or outdated/expired form) Failure to perform or follow an approved study procedure that, in the opinion of the Site investigator, does not affect subject safety or data integrity Study procedure conducted out of sequence Failure to perform a required lab test Missing lab results Study Visit out of approved window Over-enrollment Enrollment of subjects after IRB approval of the study has expired Failure to submit a continuing review application to the IRB before study expiration |

TABLE 6-continued

Major and Minor Protocol Violations

| | Major Protocol Violation | Minor Protocol Violation |
|---|---|---|
| Reporting Requirements | Record the date discovered, date occurred, description of event in the Protocol Deviation Log. Notify the Coordinating Center within 24 hours. | Record the date discovered, date occurred, description of event in the Protocol Deviation Log, Notify the Coordinating Center |

13. Treatment Regimen

Dosing

L-arginine: A fixed dose of 6 g per day, which is a commonly recommended dosage as a general nutrition supplement, will be used in this study.

BH4: For PKU patients 7 years and older, the recommended starting dose of Kuvan is 10 to 20 mg/kg taken once daily. In this study, we choose the dose of 15 mg/kg once daily.

Treatment Duration

This is the first study using L-arginine and/or BH4 supplementation in patients with schizophrenia. Previous studies have used L-arginine supplementation in other human subjects. For example, Fayh et al. reported that one-week L-arginine supplementation (7000 mg per day) improved oxidative stress status, increased blood flow and exercise responses in young adults with uncomplicated type 1 diabetes (Fayh et al 2013). In the study by Hallak et al. (Hallak et al 2013), a single 4-hour intravenous infusion of SNP, a donor of nitric oxide, led to significant improvement in positive and negative symptoms of schizophrenia at 2 hours during the infusion, and persisted for 28 days after the infusion. In this proposed trial, two weeks are felt to be reasonably enough time for L-arginine supplementation and nitric oxide to have meaningful impact on the brain, and to demonstrate "target engagement" in the brain.

15. Study Product Supplies and Administration

L-arginine: L-arginine is supplied as power for oral solution. A local compounding pharmacy Boulevard Pharmacy (Worcester, Mass.) will prepare packets of 6 g L-arginine. Subjects will take one 6 g packet, once per day in water or juice, preferably before a meal per the manufacturer's recommendation.

BH4: Kuvan is supplied as powder for oral solution containing sapropterin dihydrochloride, an orally active synthetic form of BH4. Subjects will take a total amount that is calculated based on the body weight (15 mg/kg), once per day. The packets will be prepared by Boulevard Pharmacy. Kuvan powder for oral solution is off-white to yellow in color. Kuvan should be taken with a meal to increase absorption, preferably at the same time each day. Kuvan powder for oral solution should be dissolved in 120-240 mL of water or apple juice and taken orally within 30 minutes of dissolution. Kuvan powder for oral solution may also be stirred in a small amount of soft foods such as apple sauce or pudding. Empty the contents of the packet(s) in water, apple juice, or a small amount of soft foods and mix thoroughly. The powder should dissolve completely.

16. Possible Drug Interactions

L-arginine (source of information: Medlineplus.gov): L-arginine seems to decrease blood pressure. Taking L-arginine along with anti-hypertensive medications, such as ACE inhibitors, angiotensin receptor blockers, isoproterenol, might increase the risk of hypotension. L-arginine may decrease blood sugar in people with type 2 diabetes. Taking L-arginine along with antidiabetes medications might increase the risk of hypoglycemia. L-arginine may increase blood flow. Taking L-arginine with nitrates might increase the risk of dizziness and lightheadedness. L-arginine may slow blood clotting. Taking L-arginine along with anticoagulant or antiplatelet medications might increase the risk of bruising and bleeding. L-arginine may increase potassium levels in the body. Taking L-arginine with potassium-sparing diuretics might cause hyperkalemia. Patients on those medications that may interact with L-arginine will be exclude from the study.

BH4 (source of information: Kuvan package insert): Medications that affect folate metabolism (e.g., methotrexate) may decrease endogenous BH4 levels as these medications can inhibit the enzyme dihydropteridine reductase (DHPR). Co-administering Kuvan with medications that affect NO-mediated vasorelaxation (e.g., PDE-5 inhibitors such as sildenafil, vardenafil, or tadalafil) may have additive effect to lead to a reduction in blood pressure; however, the combined use of these medications has not been evaluated in humans. In animal studies, orally administered Kuvan in combination with a PDE-5 inhibitor had no effect on blood pressure. In a 10-year post-marketing safety surveillance program for a non-PKU indication using another formulation of the same active ingredient (sapropterin), 3 patients with underlying neurologic disorders experienced confusions, exacerbation of convulsions, over-stimulation, or irritability during co-administration of levodopa and sapropterin. Folate metabolism inhibitors, PDE-5 inhibitors and levodopa are part of the exclusion criteria in this study.

17. Concomitant Therapy

The subject may not have adjustment of psychotropic medications except for benzodiazepines or anticholinergic agents if deemed absolutely necessary by the Investigator for relief of transient symptoms. Subjects must be questioned at each study visit concerning any new medications or changes in current medications including over-the-counter medication and topical medication. The subjects' antipsychotic medication type should have remained unchanged for at least eight (8) weeks prior to screening into the study, at constant dose for at least 4 weeks, and should be expected to remain unchanged during the study.

18. Discontinuation from Study Treatment

Every effort will be made to keep the patient in the study for the full study period. Acceptable reasons for early discontinuation include the following: 1) request of patient, 2) decision of the PI, 3) serious adverse event, and 4) protocol violation.

Procedures for discontinuation from study: If a patient discontinues from the study before randomization, then no further follow-up will be expected. However, if the patient discontinues after randomization, but before receiving any study treatment, the patient will be asked to return for a final study visit, during which the procedures outlined in the early termination visit procedures will be completed, including AEs and concomitant medication assessments.

If a patient discontinues from the study before completion and has received the dose of study drug, the patient will be asked to return for a final study visit, at which the procedures outlined in the early termination visit will be completed. Every effort should be made to follow up with patients who discontinue from the study. If the patient refuses follow-up, the reason for the refusal and last contact date should be documented in the CRF.

19. Ethical Considerations

Risk/Benefit Assessment

The proposed study will potentially help provide a novel treatment for individuals with schizophrenia. If this intervention is effective, these results will lead to a full clinical development program of L-arginine and BH4 combination as a treatment for schizophrenia.

The treatment has been selected with consideration of safety in mind. Additionally, exposure to the intervention will be relatively short (2 weeks) and carefully monitored. The risks of participation in the study are therefore judged to be small, and adequate protections are in place to monitor the medical wellbeing of participants.

The aforementioned data suggest that risks to subjects are minimal. The benefit to society from the development of efficacious interventions for schizophrenia would be a substantial public health benefit.

Informed Consent

The investigator must ensure that patients are clearly and fully informed about the purpose, potential risks, and other critical issues regarding clinical trials in which they volunteer to participate. Preparation of the consent form is the responsibility of the investigator and must include all elements required by CFR 21 Part 50.25 and the UMass IRB.

All subjects will receive the consent form for the study. Any questions, concerns, or ambiguities will be clarified by the PI or medically qualified designee prior to the patient signing consent. Subjects will sign informed consent and only then will begin participation in the study.

Independent Safety and Data Monitoring

The inclusion and exclusion criteria, and the eligibility to participate in the study will be reviewed and determined independently by a board-certified psychiatrist other than the PI. The same independent psychiatrist will review all adverse events and outcome measure data throughout the conduct of the study.

IRB Review

Before study initiation, the investigator must have written and dated approval/favorable opinion from the UMass IRB for the protocol, consent form, patient recruitment materials and process (e.g., advertisements), and any other written information to be provided to subjects.

The investigator should provide the IRB with reports, updates, and other information (e.g., safety updates, amendments) according to regulatory requirements and institution procedures.

20. Data Handling and Record Keeping

Study specific data that has been outlined in the protocol will be entered into the clinical database via the electronic data capture (EDC) system by designated research staff in accordance with the eCRF Completion Guidelines. Data is verified electronically using a series of on-line programmed edit checks that have been created by the clinical data manager and programmed by the clinical data programmer or designee. Data discrepancies will be brought to the attention of the PI, and investigated by the research staff until resolutions can be made.

Database Quality Assurance

The clinical database will be reviewed and checked for omissions, apparent errors, and values requiring further clarification using computerized and manual procedures. Only authorized personnel will make corrections to the clinical database, and all corrections will be documented.

Record Retention

All documents pertaining to the study, including all versions of the approved study protocol, copy of the informed consent document and Health Insurance Portability and Accountability Act (HIPAA) documents, eCRFs, source documents (i.e., subject records, hospital records, laboratory records, medication records, etc.), and other study-related documents will be retained for 5 years after the study ends.

Data Confidentiality

Potential risks to data confidentiality will be mitigated by requirements for the de-identification of all study data and by security protocols for all data capture systems. All users of the EDC system will be tracked and provided access in a secure fashion following established SOPs for this process.

As with all research data, information gathered by the study will be used only for aggregate analysis; it will not be released with any information that identifies research participants. Uses and risks related to data collection will be outlined in the informed consent and reviewed with the subjects.

21. Data Analysis

There are no published data yet about the effect of the L-arginine and BH4 combination treatment on schizophrenia symptoms. This study is intended as a pilot trial of feasibility, acceptability, safety, tolerability. In addition, the study is intended to provide preliminary evidence of target engagement in the brain, as well as an indication of effect size for the purpose of designing future studies. Paired sample t tests will be used to examine the difference in outcome measures between week 2 and baseline. In addition, Pearson correlation analysis or partial correlation analysis will be used to examine the relationship between changes in NO bioavailability or blood biomarkers and changes in symptom outcome measures.

I claim:

1. A method, comprising:
a) providing:
i) a patient comprising an uncoupled nitric oxide synthase pathway, and exhibiting at least one symptom of a neuropsychiatric disorder; and
ii) a pharmaceutical composition comprising L-arginine and tetrahydrobiopterin;
b) administering said pharmaceutical composition to said patient under conditions such that said uncoupled nitric oxide synthase pathway converts to a coupled nitric oxide synthase pathway and said at least one symptom of a neuropsychiatric disorder is reduced.

2. The method of claim 1, wherein said uncoupled nitric oxide synthase pathway underproduces nitric oxide.

3. The method of claim 1, wherein said uncoupled nitric oxide synthase pathway overproduces superoxide, hydrogen peroxide and peroxynitrite.

4. The method of claim 3, wherein said superoxide, hydrogen peroxide and peroxynitrite confers neurotoxicity and induces said at least one symptom of a neuropsychiatric disorder.

5. The method of claim 1, wherein said coupled nitric oxide synthase pathway produces a homeostatic level of nitric oxide.

6. The method of claim 5, wherein said homeostatic level of nitric oxide confers neuroprotection.

7. The method of claim 1, wherein said coupled nitric oxide synthase pathway produces minimal levels of superoxide, hydrogen peroxide and peroxynitrite.

8. The method of claim 5, wherein said homeostatic level of nitric oxide confers neuroplasticity.

9. The method of claim 1, wherein staid neuropsychiatric disorder is schizophrenia.

10. The method of claim 1, wherein said neuropsychiatric disorder is depression.

11. The method of claim 1, wherein said neuropsychiatric disorder is bipolar disorder.

12. The method of claim 1, wherein said neuropsychiatric disorder is delusion.

13. The method of claim 1, wherein said neuropsychiatric disorder is selected from the group consisting of schizotypal personality disorder, delusional disorder, brief neuropsychiatric disorder, schizophreniform disorder, schizoaffective disorder, substance/medication-induced neuropsychiatric disorder, neuropsychiatric disorder due to another medical condition, catatonia, depressive disorders and bipolar and related disorders.

14. The method of claim 1, wherein said uncoupled nitric acid synthase pathway is an uncoupled endothelial nitric acid synthase pathway.

15. The method of claim 1, wherein said patient further comprises a blood brain barrier.

16. The method of claim 15, wherein said pharmaceutical composition crosses said blood brain barrier.

17. The method of claim 1, wherein said tetrahydrobiopterin is naturally occurring.

18. The method of claim 1, wherein said tetrahydrobiopterin is sapropterin dihydrochloride.

* * * * *